US011401500B2

(12) United States Patent
Greenwald et al.

(10) Patent No.: US 11,401,500 B2
(45) Date of Patent: Aug. 2, 2022

(54) SYSTEM, METHOD, AND COMPOSITION FOR INCUBATING SPORES FOR USE IN AQUACULTURE, AGRICULTURE, WASTEWATER, AND ENVIRONMENTAL REMEDIATION APPLICATIONS

(71) Applicant: NCH Corporation, Irving, TX (US)

(72) Inventors: Charles Greenwald, Irving, TX (US); Ivy Jones, Coppell, TX (US); John Knope, Flower Mound, TX (US)

(73) Assignee: NCH Corporation, Irving, TX (US)

( * ) Notice: Subject to any disclaimer, the term of this patent is extended or adjusted under 35 U.S.C. 154(b) by 349 days.

(21) Appl. No.: 16/549,140

(22) Filed: Aug. 23, 2019

(65) Prior Publication Data
US 2020/0071661 A1 Mar. 5, 2020

Related U.S. Application Data

(60) Provisional application No. 62/724,392, filed on Aug. 29, 2018.

(51) Int. Cl.
C12N 1/20 (2006.01)
C02F 3/34 (2006.01)
A47J 36/28 (2006.01)

(52) U.S. Cl.
CPC .............. C12N 1/20 (2013.01); C02F 3/34 (2013.01); C02F 3/341 (2013.01); A47J 36/28 (2013.01);
(Continued)

(58) Field of Classification Search
CPC .. C02F 3/34; C02F 3/006; C02F 3/348; C02F 3/341; C02F 2301/106; C02F 2203/004;
(Continued)

(56) References Cited

U.S. PATENT DOCUMENTS 3,203,870 A * 8/1965 John ............... C12M 23/10
435/305.4
4,294,924 A * 10/1981 Pepicelli ............ C12Q 1/06
215/10
(Continued)

FOREIGN PATENT DOCUMENTS

CN 1528681 9/2004
CN 102387703 3/2012
(Continued)

OTHER PUBLICATIONS

American Society of Agronomy (ASA), Crop Science Society of America (CSSA). "Probiotics—for plants." ScienceDaily ScienceDaily, Jul. 8, 2015 Jul. 8, 2015.
(Continued)

Primary Examiner — Sean C. Barron
(74) Attorney, Agent, or Firm — Scheef & Stone, LLP; Robin L. Barnes

(57) ABSTRACT

A system and method for generating an incubated bacteria solution by heating a nutrient germinant composition and bacteria, including at least one species in spore form, to a preferred temperature a range of 35-50° C. for 2-60 minutes using exothermic chemical reaction heat. An incubated bacteria solution is preferably generated at or near a point-of-use in an aquaculture, agriculture, wastewater, or environmental remediation application. The nutrient-germinant composition comprises L-amino acids, optionally D-glucose and/or D-fructose, a buffer, an industrial preservative, and may include bacteria spores (preferably of one or more *Bacillus* species) or they may be separately combined for incubation. A first chemical contained in a pouch is activated by contact with a second chemical, water, or air in a flameless heater to initiate exothermic reaction to provide incubation heat. A potable, single-use incubation bag is
(Continued)

configured to hold the flameless heater and a container of nutrient germinant composition and spores.

30 Claims, 7 Drawing Sheets

(52) U.S. Cl.
CPC .... *C02F 2301/106* (2013.01); *C12N 2500/32* (2013.01); *C12N 2500/33* (2013.01); *C12N 2500/34* (2013.01); *C12N 2500/60* (2013.01)

(58) Field of Classification Search
CPC .. C12N 1/20; C12N 2500/33; C12N 2500/34; C12N 2500/60; C12N 2500/32; A47J 36/28
See application file for complete search history.

(56) References Cited

U.S. PATENT DOCUMENTS

| | | |
|---|---|---|
| 4,314,995 A | 2/1982 | Hata et al. |
| 4,840,792 A | 6/1989 | Joulain et al. |
| 4,872,985 A | 10/1989 | Dinges |
| 4,910,024 A | 3/1990 | Pratt |
| 4,919,936 A | 4/1990 | Iwanami et al. |
| 4,995,980 A | 2/1991 | Jaubert |
| 4,999,193 A | 3/1991 | Nguyen |
| 5,093,121 A | 3/1992 | Kvanta et al. |
| 5,154,594 A | 10/1992 | Gamlen |
| 5,292,523 A | 3/1994 | Kono et al. |
| 5,320,256 A | 6/1994 | Wood |
| 5,413,713 A | 5/1995 | Day et al. |
| 5,501,857 A | 3/1996 | Zimmer |
| 5,611,329 A | 3/1997 | Lamensdorf |
| 5,702,604 A | 12/1997 | Yamasaki et al. |
| 5,821,112 A | 10/1998 | Botto et al. |
| 5,935,486 A * | 8/1999 | Bell ............ C09K 5/18 252/70 |
| 5,968,569 A | 10/1999 | Cavadini et al. |
| 6,051,219 A | 4/2000 | Kubota |
| 6,254,910 B1 | 7/2001 | Paluch |
| 6,308,658 B1 | 10/2001 | Steckel |
| 6,312,746 B2 | 11/2001 | Paluch |
| 6,327,965 B1 | 12/2001 | Tien |
| 6,335,191 B1 | 1/2002 | Kiplinger et al. |
| 6,341,602 B1 * | 1/2002 | Fulcher ............ A47J 36/28 126/263.07 |
| 6,382,132 B1 | 5/2002 | Steckel et al. |
| 6,461,607 B1 | 10/2002 | Farmer |
| 6,498,137 B1 | 12/2002 | Schalitz et al. |
| 6,723,076 B1 | 4/2004 | Strobel |
| 6,827,957 B2 | 12/2004 | Paluch et al. |
| 6,849,256 B1 | 2/2005 | Farmer |
| 7,081,361 B2 | 7/2006 | Pearce, III et al. |
| 7,485,466 B2 | 2/2009 | Jenkins et al. |
| 7,635,587 B2 | 12/2009 | Pearce, III et al. |
| 7,670,845 B2 | 3/2010 | Wenzel et al. |
| 7,713,726 B2 | 5/2010 | Farmer |
| 7,736,509 B2 | 6/2010 | Kruse |
| 7,754,469 B2 | 7/2010 | Baltzley et al. |
| 8,025,847 B2 | 9/2011 | Fouarge et al. |
| 8,025,874 B2 | 9/2011 | Bellot et al. |
| 8,062,528 B2 * | 11/2011 | Back ............ C02F 1/44 210/652 |
| 8,062,902 B2 | 11/2011 | Mestrallet |
| 8,093,040 B2 | 1/2012 | Pearce, III et al. |
| 8,192,733 B2 | 6/2012 | Cobb et al. |
| 8,277,799 B2 | 10/2012 | Farmer |
| 8,349,337 B1 | 1/2013 | Farmer et al. |
| 8,404,227 B2 | 3/2013 | Bellot et al. |
| 8,506,951 B2 | 8/2013 | Rehberger et al. |
| 8,540,981 B1 | 9/2013 | Wehnes et al. |
| 8,551,762 B2 | 10/2013 | Fleming et al. |
| 8,647,690 B2 | 2/2014 | Corrigan |
| 8,822,208 B2 | 9/2014 | Chokshi |
| 9,011,834 B1 | 4/2015 | Mckenzie et al. |
| 9,447,376 B2 | 9/2016 | Hashman et al. |
| 9,908,799 B2 | 3/2018 | Greenwald et al. |
| 10,744,469 B2 | 8/2020 | Breidenthal et al. |
| 10,766,799 B2 | 9/2020 | Greenwald et al. |
| 2001/0031276 A1 | 10/2001 | Shelford |
| 2003/0031659 A1 | 2/2003 | Farmer |
| 2003/0165472 A1 | 9/2003 | McGrath et al. |
| 2004/0232069 A1 | 11/2004 | Shaffer |
| 2005/0164902 A1 * | 7/2005 | Man ............ C11D 3/30 510/503 |
| 2005/0255092 A1 | 11/2005 | Rehberger et al. |
| 2006/0093591 A1 | 5/2006 | Farmer et al. |
| 2006/0275324 A1 | 12/2006 | Elston et al. |
| 2008/0107699 A1 | 5/2008 | Spigelman et al. |
| 2008/0241226 A1 | 10/2008 | Abeln et al. |
| 2009/0041898 A1 | 2/2009 | Garbolino et al. |
| 2009/0111694 A1 | 4/2009 | Dituro |
| 2009/0186057 A1 | 7/2009 | Farmer et al. |
| 2009/0232941 A1 | 9/2009 | Farmer |
| 2009/0242173 A1 | 10/2009 | Mitchell |
| 2010/0089381 A1 | 4/2010 | Bolmer et al. |
| 2010/0124586 A1 | 5/2010 | Becker |
| 2010/0261226 A1 | 10/2010 | Niazi |
| 2011/0020914 A1 | 1/2011 | Abu-Nemeh |
| 2011/0189132 A1 | 8/2011 | Garner et al. |
| 2011/0230345 A1 | 9/2011 | Snyder et al. |
| 2011/0256216 A1 | 10/2011 | Lefkowitz |
| 2012/0034344 A1 | 2/2012 | Menon |
| 2012/0052152 A1 | 3/2012 | Armentrout |
| 2012/0100094 A1 | 4/2012 | Reuter et al. |
| 2012/0296075 A1 | 11/2012 | Reed et al. |
| 2013/0017174 A1 | 1/2013 | Hargis et al. |
| 2013/0092087 A1 | 4/2013 | Bachman et al. |
| 2013/0171204 A1 | 7/2013 | DuBourdieu |
| 2013/0202562 A1 | 8/2013 | Wood |
| 2014/0220662 A1 | 8/2014 | Hashman |
| 2015/0079661 A1 | 3/2015 | Pruitt |
| 2015/0118203 A1 | 4/2015 | Boyette et al. |
| 2015/0139970 A1 * | 5/2015 | Tategaki ............ A61P 1/00 424/93.48 |
| 2015/0147808 A1 * | 5/2015 | Vacher ............ C12M 23/10 435/380 |
| 2015/0299636 A1 | 10/2015 | Virtanen et al. |
| 2015/0333828 A1 | 11/2015 | Greenwald et al. |
| 2017/0042949 A1 | 2/2017 | Penaloza-Vazquez |
| 2017/0087199 A1 | 3/2017 | Patron |
| 2017/0175070 A1 | 6/2017 | Boyette et al. |
| 2017/0246222 A1 | 8/2017 | Lewis |
| 2017/0281696 A1 | 10/2017 | Everett et al. |
| 2018/0282685 A1 | 10/2018 | Pruitt |
| 2019/0071336 A1 | 3/2019 | Greenwald et al. |
| 2019/0098915 A1 | 4/2019 | Church et al. |
| 2019/0100723 A1 | 4/2019 | Church et al. |
| 2020/0078751 A1 | 3/2020 | Schuster |

FOREIGN PATENT DOCUMENTS

| | | |
|---|---|---|
| CN | 105060980 | 11/2015 |
| EP | 0410877 | 1/1991 |
| EP | 0826311 | 3/1998 |
| EP | 0885557 | 8/2004 |
| JP | 5724217 | 5/2015 |
| KR | 100865682 | 10/2008 |
| WO | WO1999005310 | 2/1999 |
| WO | WO2000033854 | 6/2000 |
| WO | WO2002051264 | 7/2002 |
| WO | WO2004024865 | 3/2004 |
| WO | WO2006002495 | 1/2006 |
| WO | WO2008071930 | 6/2008 |
| WO | WO2009040445 | 4/2009 |
| WO | WO2009117790 | 10/2009 |
| WO | WO2009126473 | 10/2009 |
| WO | WO2010003255 | 1/2010 |
| WO | WO2010020639 | 2/2010 |
| WO | WO2010045541 | 4/2010 |
| WO | WO2010066012 | 6/2010 |
| WO | WO2010079104 | 7/2010 |

(56) References Cited

FOREIGN PATENT DOCUMENTS

| WO | WO2010088744 | | 8/2010 | | |
|---|---|---|---|---|---|
| WO | WO2010142004 | | 12/2010 | | |
| WO | WO2011056487 | | 5/2011 | | |
| WO | WO2012027214 | | 3/2012 | | |
| WO | WO2012079973 | | 6/2012 | | |
| WO | WO2012108830 | | 8/2012 | | |
| WO | WO2012167882 | | 12/2012 | | |
| WO | WO2013119493 | | 8/2013 | | |
| WO | WO2013142792 | | 9/2013 | | |
| WO | WO2013191642 | | 12/2013 | | |
| WO | WO2014083177 | | 6/2014 | | |
| WO | WO2014193746 | | 12/2014 | | |
| WO | WO-2014193746 | A1 * | 12/2014 | ............ | C12N 1/205 |
| WO | WO2015038892 | | 3/2015 | | |
| WO | WO2015179788 | | 11/2015 | | |
| WO | WO2016022779 | | 2/2016 | | |
| WO | WO2016044661 | | 3/2016 | | |
| WO | WO-2016170086 | A1 * | 10/2016 | ............ | C12M 27/16 |
| WO | WO2017117089 | | 7/2017 | | |
| WO | WO2019168627 | | 9/2019 | | |
| WO | WO2020212384 | | 10/2020 | | |

OTHER PUBLICATIONS

Balcazar et al., The role of probiotics in aquaculture, Veterinary microbiology 114.3, 173-186, 2006 Jan. 17, 2006.
Bentzon-Tilia et al., Monitoring and Managing Microbes in Aquaculture-Towards a sustainable industry, Microbial biotechnology 9.5, 576-584, 2016 Apr. 24, 2016.
Farzanfar, The use of probiotics in shrimp aquaculture, FEMS Immunology & Medical Microbiology 48.2, 149-158, 2006 Apr. 20, 2006.
Hai, The use of probiotics in aquaculture, Journal of applied microbiology 119.4, 917-935, 2015 Jun. 22, 2015.
Joint FAO/WHO Expert Consultation on Evaluation of health and nutritional properties of probiotics in food including powder milk with live lactic acid bacteria, Cordoba, Argentina. Oct. 1-4, 2001 Oct. 1, 2001.
Kumar et al., Bacillus as PGPR in crop ecosystem; Bacteria in agrobiology: crop ecosystems. Springer Berlin Heidelberg, 37-59, 2011 2011.
Lakshmi et al., Probiotics as antiviral agents in shrimp aquaculture, Journal of pathogens 2013 Apr. 9, 2013.
Mahdhi et al., Survival and retention of the probiotic properties of Baccilus sp. strains under marine stress starvation conditions and their potential use as a probiotic in Artemia culture, Research in veterinary science 93.3, 1151-1159, 2012 Dec. 2012.
Sahu et al., Probiotics in aquaculture: importance and future perspectives. Indian journal of microbiology 48.3, 299-308 2008 Jun. 13, 2008.
Soni et al., Safety Assessment of Propyl Paraben: a review of the published literature, Food and Chemical Toxicology vol. 39, 2001, p. 513-532.
Mohan, Chandra, A guide for the preparation and use of buffers in biological systems, CalBiochem Buffers, 2003; http://www.antibodybeyond.com/books/Calbiochem_Buffers_Booklet_CB0052_E.pdf; retrieved Mar. 8, 2020.
Nguyen, Bacillus subtilis spores expressing the VP28 antigen; a potential oral treatment to protect Litopenaeus vannamei against white spot syndrome, FEMS Microbiilogy Letters 01, Sep. 2014 (Sep. 1, 2014), vol. 358, pp. 202-208, p. 203.
Shearer et al., Bacterial Spore Inhibition and Inactivation in Foods by Pressure, Chemical Preservatives, and Mild Heat, Journal of Food Protection, Nov. 2000, vol. 63, pp. 1503-1510, p. 1504-1505.
Setlow, Germination of Spores of Bacillus Species, What We Know and Do Not Know, Journal of Bacteriologoy, Apr. 2014, vol. 196, pp. 1297-1305, p. 1298.
Safe Feeding with Lupro-Grain and Amasil NA—product brochure available from BASF Chemical Company, published at least as early as 2011, Retrieved, from the Internet on Feb. 16, 2015 at <URL: http://www.basfanimalnutrition.de/downloads/an_safe_feeding_en.pdf and http://www.basfanimalnutrition.de/en/news_2008_09_09.php>.
Supporting More Sustainable Livestock Production Luprosil & Amasil Less Spoilage, Improved Hygiene, product brochure from BASF Chemical Company, believed published at least as early as 2011, Retrieved from the Internet on Feb. 16, 2015 at <URL: http://www.newtrition.basf.com/web/global/de/function/conversions:/publish/content/microsites/animal-nutrition/Sustainability_Contribution/assets/Luprosil_Amasil. pdf>.
Bactocell Drink is Now Authorized in Europe as a Feed Additive for Swine and Poultry, news release from Lallemand Animal Nutrition, published May 15, 2013, Retrieved from the Internet on Feb. 16, 2016 at <URL: http://lallemandanimalnutrition.com/news/bactocell-drink-is-now-authorized-in-europe-as-a-feed-additive-for-swine-and-poultry/>.
Bactocell Drink on-tracks for EU authorization as a feed additive for use in drinking water for swine and poultry, news release from Lallemand Animal Nutrition, published Aug. 29, 2012, Retrieved from the Internet on Feb. 16, 2016 at <URL: http ://1 al lerna nda n i m a In utritio n. com/ news/bactocel 1-d rink-a n-tracks-fo r-eu-a uthorizati on-as-a-feed- additive-for -use-i n-d rinking-water -for-swine-and-poultry/>.
European Food Safety Authority Scientific Opinion on the Safety and Efficacy of Bactocell, published in the EFSA Journal 2012; 10(7):2776, Retrieved from the Internet on Feb. 16, 2016 at <URL: http://www.efsa.europa.eu/sites/default/files/scientific_output/files/main_documents/2776.pdf>.
Biotic for Poultry and Swine—product information available from Biopharmachemie, believed to be published at least as early as 2011, Retrieved from the Internet on Feb. 16, 2016 at <URL: http://www.biopharmachemie.com/product/products-for-l ivestock/b i otic. him l>.
Calsporin Swine FAQ, product information available from Quality Technology International, Inc., published 2012, Retrieved from the Internet on Feb. 16, 2016 at <URL: http://www.qtitechnology.com/sites/default/files/pdfs/CalsporinSwineFAQ.pdf>.
Calsporin Poultry FAQ, product information available from Quality Technology International, Inc., published 2012, Retrieved from the Internet on Feb. 16, 2016 at <URL: http://www.qtitechnology.com/sites/default/files/pdfs/CalsporinPoultryFAQ.pdf>.
Proftora Live DFM: Bacillus Subtilis Strain QST 713, product information available from Zoetis, believed to be published at least as early as 2013, Retrieved from the Internet on Feb. 16, 2016 at <URL: https://www.zoetisus.com/ products/poultry Ip rofto ra. as px>.
BioGrow, product Information available from Provita, believed to be published at least as early as 2013 (BioGrow product available since 2001), Retrieved from the Internet on Feb. 16, 2016 at <URL: http://www.provita.co.uk/poultry/biogrow>.
Chorawala, M. R., P. M. Oza, G. B. Shah. 2011. Probiotics, Prebiotics and Synbiotics: A Health Benefit Supplement. Research Journal of Pharmaceutical, Biological and Chemical Sciences vol. 2 (3): 1101-1111.
Amerah, A.M., C. J. van Rensburg, P. W. Plumstead, C. Kromm, and S. Dunham. 2013. Effect of feeding diets containing a probiotic or antibiotic on broiler performance, intestinal mucosa-associated avian pathogenic E. coli and litter water-soluble phosphorus. Journal of Applied Animal Nutrition, vol. 1; E 7.
Sutton, A. L., K. B. Kephart, M. W. A. Verstegen, T. T. Canh, and P. J. Hobbs. Potential for reduction of odorous compounds in swine manure through diet modification. Journal of Animal Science, 1999, 77:430-439.
Davis, M. E., T. Parrott, D. C. Brown, B. Z. de Rodas, Z. B. Johnson, C. V. Maxwell, T. Rehberger. 2008. Effect of a Bacillus-based direct-fed microbial feed supplement on growth performance and pen cleaning characteristics of growing-finishing pigs. Journal of Animal Science, 2008; 86:1459-1467.
Balcazar, The role of probiotics in aquaculture, Veterinary Microbiology, 114.3, 173-186, 2006.
Bentzon-Tilia, Monitoring and manafging microbes in aquaculture—towards sustainable industry, Microbila Biotechnology, 9.5, 576-584, 2016.

(56) References Cited

OTHER PUBLICATIONS

Farzanfar, The use of probiotics in shrimp aquaculture, FEMS Immunology & Medical Microbiology, 48.2, 149-159, 2006.
Hai, The use of probiotics in aquaculture, Journal of applied microbiology, 119.4, 917-935, 2015.
Kumar, Bacillus as PGPR in crop ecosystem, Bacteria in agrobiology: crop ecosystems, Springer Berlin Heidelberg, 37-59, 2011.
Lakshmi, Probiotics as antiviral agents in shrimp aquaculture, Journal of Pathogens 2013.
Mahdhi, Survival and retention of the probiotic properties of Bacillus sp. Strains under marine stress starvation conditiona dn their potential use as a probiotic in Artemia culture, Research in veterinary science 93.3, 1151-1159, 2012.
Sahu, Probiotics in Aquaculture: importance and future perspectives Indian Journal of microbiology 48.3, 299-308, 2008.
Mitsuhashi T "Effects of and L-alanine on the Swelling of Bacillus subtilis spores during germination" —Nippon suisan Gakkaishi—Bulletin of Japanese Society of Scientifici Fisheries, vol. 59, No. 5 1993 pp. 841-846.
Bader J "Spore-forming bacteria and their utilisation as probiotics" Beneficial Microbes, vol. 3, No. 1, Mar. 1, 2012 pp. 67-75.
Timmermann et al., Metabolism and Nutrition Mortality and Growth Performance of Broilers Given Drinking Water Supplemented with Chicken-Specific Probiotics, Poultry Science, vol. 85, Aug. 1, 2006, pp. 1383-1388.
Katsutoshi et al., Effect of spore-bearing lactic acid-forming bacteria (Bacillus coagulans SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp. 4-13.
El-Mougy, Application of Fungicides Alternatives as Seed Treatment for Controlling Root Rot of Some Vegetables in Pot Experiments. Advances in Life Sciences 2012, 2(3):57-64.
Yeo, et al., Antihypertensive Properties of Plant-Based Prebiotics. Int. J. Mol. Sci. 2009, 10, 3517-3530.
He, et al., Effects of Trehalose, Glycerin and NaCl on the Growth and Freeze-Drying of Lactobacillus acidophilus. Information Technology and Agricultural Engineering. 2012; 967-971.
Safe Feeding with Lupro-Grain and Amasil NA—product brochure available from BASF Chemical Company, published at least as early as 2011, Retrieved, from the Internet on Feb. 16, 2016 at <URL: http://www.basfanimalnutrition.de/downloads/an_safe_feeding_en.pdf and http://www.basfanimalnutrition.de/en/news_2008_09_09.php.
Supporting More Sustainable Livestock Production Luprosil & Amasil Less Spoilage, Improved Hygiene, product brochure from BASF Chemical Company, believed published at least as early as 2011, Retrieved from the Internet on Feb. 16, 2016 at <URL: http://www.newtrition.basf.com/web/global/de/function/conversions:/publish/content/microsites/animal-nutrition/Sustainability_Contribution/assets/Luprosil_Amasil. pdf.
Activate & Activate WD Max Product Information available from Nevus, believed published at least as early as 2011, Retrieved from the Internet on Feb. 16, 2016 at http://novusintqa.enlivenhq.com/Products/activate#fndtn-activatewdmax.
Bactocell Drink is Now Authorized in Europe as a Feed Additive for Swine and Poultry, news release from Lallemand Animal Nutrition, published May 15, 2013, Retrieved from the Interneton Feb. 16, 2016 at <URL: http://Tallemandanimalnutrition.com/news/bactocell-drink-is-now-authorized-in-europe-as-a-feed-additive-for-swine-and-poultry/.
Bactocell Drink on-tracks for EU authorization as a feed additive for use in drinking water for swine and poultry, news release from Lallemand Animal Nutrition, published Aug. 29, 2012, Retrieved from the Internet on Feb. 16, 2016 at <URL: http ://1 al lerna nda n i rn a In utritio n. com/ news/bactocel 1-d rink-a n-tracks-fo r-eu-a uthorizati on-as-a-feed- additive-for -use-i n-d rinking-water -for-swine-and-poultry/.

Feed Preservation with formic acid from BASF, product information available from BASF Chemical Company, believed to be published at least as early as 2011, Retrieved from the Internet on Feb. 16, 2016 at <URL: http://www.intermediates.basf.com/chemicals/formic-acid/feed-preservation.
The Great Preserver—Propionic Acid protects food and animal feed from mold—rising demand, product information available from BASF Chemical Company, believed to be published at least as early as 2011, Retrieved from the Internet on Feb. 16, 2016 at <URL: http://www.intermediates.basf.com/chemicals/topstory/propionsaeure.
Organic Acids, product information available from BASF Chemical Company, believed to be published at least as early as 2011, Retrieved from the Internet on Feb. 16, 2016 at <URL: http://www.animal-nutrition.basf.com/web/global/animal-nutrition/en_GB/Products/OrganicAcids/index.
Poultry Product Quality—product information regarding BioPlus available from Chr. Hansen, believed to be published at least as early as 2011, Retrieved from the Internet on Feb. 16, 2016 at <URL: http://www.chr-hansen.com/animal-probiotics-and-silage-inoculants/probiotics-for-poultry/poultry-product-quality.
European Food Safety Authority Scientific Opinion on the Safety and Efficacy of BioPlus 2B, published in the EFSA Journal 2011; 9(9):2356, Retrieved from the Internet on Feb. 16, 2016 at <URL: http://www.efsa.europa.eu/sites/default/files/scientific_output/files/main_documents/2356.pdf.
Biotic for Shrimp—product information available from Biopharmachemie, believed to be published at least as early as 2011, Retrieved from the Internet on Feb. 16, 2016 at <URL: http://biopharmachemie.com/product/products-for-shrimp/biotic-for-shrimp.html.
Biozyme for Shrimp—product information available from Biopharmachemie, believed to be published at least as early as 2011, Retrieved from the Internet on Feb. 16, 2016 at <URL: http://biopharmachemie.com/product/products-for-shrimp/biozyme-for-shrimp.html.
Biotic for Poultry and Swine—product information available from Biopharmachemie, believed to be published at least as early as 2011, Retrieved from the Internet on Feb. 16, 2016 at <URL: http://www.biopharmachemie.com/product/products-for-I ivestock/b i otic. him I.
Dosatron Water Powered Dosing Technology D 25 Range—product brochure available from Dosatron International, published 2007, Retrieved from the Internet on Feb. 16, 2016 at <URL: https:1/bd.dosatron.com/Products_Produits/RangeSheets_FichesGamme/D25/Rangesheet_FichesGamme_D25_EN.pdf.
Delivering superior swine performance—product information on VevoVitall available from DSM, believed to be published at least as early as 2011, Retrieved from the Internet on Feb. 16, 2016 at <URL: http://www.dsm.com/marketslanh/en_US/products/products-eubiotics/products-eubiotics-vevovitall.html.
Selko-pH Health Promoter water, Three Steps to Improve intestinal health via drinking water, product information available from Seiko, believed to be published at least as early as 2011, Retrieved from the Internet on Feb. 16, 2016 at <URL: http://www.amcra.be/sites/default/files1Jaco%20Eisen%20Selko%20Feed%20Additives.pdf.
Selko-PH, product information available from Seiko, believed to be published at least as early as 2011, Retrieved from the Internet on Feb. 16, 2016 at <URL: http://www.selko.com/en/products/selko-ph/9129.
FloraMax B-11, (Tech Sheet) product information available from Ivesco, believed to be published at least as early as 2011 (product available since 2004), Retrieved from the Internet on Feb. 16, 2016 at <URL: http://www.ivescopoultry.com/Attachment/5/20535_5_FloraMaxTechSheet.pdf.
FloraMax B-11 Proven in the lab . . . confirmed in the field, product information available from Pacific Vet Group, believed to be published at least as early as 2011 (product available since 2004), Retrieved from the Internet on Feb. 16, 2016 at <URL: http://www.pacificVetgroup.com/docs/PVG-FloraMaxB-11.pdf.
Fortify Liquid Concentrated Direct-Fed Microbial for Drinking Water, product label available from Assist Natural Products and Services, LLC, believed to be published at least as early as 2013,

(56) References Cited

OTHER PUBLICATIONS

Retrieved from the Internet on Feb. 16, 2016 at <URL: http://www.assist-nps.com/files/Fortify%20Liquid%20Label.pdf.
Cutting, Simon M., Bacillus Probiotics, Food Microbiology, 2011, vol. 28, pp. 214-220.
Kem San Brand Liquid Antimicrobial, product specification available from Kem in Vet Innovations, Inc., 2100 Maury Street, Des Moines, Iowa 50317, published 2011.
Optimizer Proven in the lab . . . confirmed in the field, product brochure available from Pacific Vet Group-USA, Inc., 2135 Creek View Drive, Fayetteville, Arkansas 72704, published 2011.
Calsporin, product information available from Calpis Co., Ltd., 4-1, Ebisu-Minami 2-chome Shibuya, Tokyo, Japan, believed to be published at least as early as 2013 (product available since at least 2000).
Calsporin Swine FAQ, product information available from Quality Technology International, Inc., published 2012, Retrieved from the Internet on Feb. 16, 2015 at <URL: http://www.qtitechnology.com/sites/default/files/pdfs/CalsporinSwineFAQ.pdf.
Calsporin Poultry FAQ, product information available from Quality Technology International, Inc., published 2012, Retrieved from the Internet on Feb. 16, 2015 at <URL: http://www.qtitechnology.com/sites/default/files/pdfs/CalsporinPoultryFAQ.pdf.
Proflora Live DFM: Bacillus Subtilis Strain QST 713, product information available from Zoetis, 100 Campus Drive, Florham Park, New Jersey 07932, believed to be published at least as early as 2013.
Proflora Live DFM: Bacillus Subtilis Strain QST 713, product information available from Zoetis, believed to be published at least as early as 2013, Retrieved from the Internet on Feb. 16, 2015 at <URL: https://www.zoetisus.com/products/poultry Ip rofto ra. as px.
BioGrow & Provita Gameguard, product information available from Provita Eurotech Limited, 21 Bankmore Road, Omagh, County Tyrone, Northern Ireland, believed to be published at least as early as 2013 (BioGrow product available since 2001).
Biogrow, product information available from Provita, believed to be published at least as early as 2013 (BioGrow product available since 2001), Retrieved from the Internet on Feb. 16, 2015 at <URL: http://www.provita.co.uk/poultry/biogrow.
Swine Bluelite 2Bw a water soluble acidified electrolyte product with probiotics for pigs, product information available from TechMix Global, published Sep. 2011, Retrieved from the Internet on Feb. 16, 2016 at <URL: https://web.archive.org/web/20110909124607/http://www.techmixglobal.com/swine-bluelite-2bw.
Swine Bluelite 2Bw a water soluble acidified electrolyte product with probiotics for pigs, product information available from TechMix Global, believed to published at least as early as 2013 (product available since 2011), Retrieved from the Internet on Feb. 16, 2015 at <URL: https://www.techmixglobal.com/swine-bluelite-2bw.
Swine Bluelite 2Bw a water soluble acidified electrolyte product with probiotics for pigs, product information available from TechMix Global, 740 Bowman St., Stewart, MN, believed to published at least as early as 2013 (product available since 2011).
Chorawala, M. R., P. M. Oza, G. B. Shah. Probiotics, Prebiotics and Synbiotics: A Health Benefit Supplement. Published Jul.-Sep. 2011 by the Research Journal of Pharmaceutical, Biological and Chemical Sciences vol. 2, Issue 3, pp. 1101-1111.
Sekhon, B. S. and J. Saloni. 2010. Prebiotics, probiotics and synbiotics: an overview. Journal of Pharmaceutical Education and Research. 1:13-36.
Patterson, J.A., K. M. Burkholder. 2003. Application of prebiotics and probiotics in poultry production. Poultry Science 82:627-631.
ADM Animal Nutrition, Direct Fed Microbial: Application and Usage Data Sheet, retrieved on Jan. 16, 2017 from http://www.admani.com/animalhealth/techbulletins/animal direct.
Casula, G and S. Cutting. Bacillus Probiotics: Spore Germination in the Gastrointestinal Tract. Published May 2002 by the American Society for Microbiology in Applied and Environmental Microbiology vol. 68, No. 5: 2344-2352.

Amerah, A.M., C. J. van Rensburg, P. W. Plumstead, C. Kromm, and S. Dunham. 2013. Effect of feeding diets containing a probiotic or antibiotic on broiler performance, intestinal mucosa-associated avian pathogenic E. coli and litter water-soluble phosphorus. Journal of Applied Animal Nutrition.
Sutton, A.L. et al., Potential for Reduction of Odorous Compounds in Swine Manure Through Diet Modification, Published in 1999 by the American Society of Animal Science in the Journal Anim. Sci. 1999, 77:430-439.
Davis M.E. et al. Effect of a Bacillus-based direct-fed microbial feed supplement on growth performance and pen cleaning characteristics of growing-finishing pigs, Published in 2008 y the American Society of Animal Sciences in the Journal of Anim. Sci. 2008, 86:1459-1467.
Sutton, A. L., K. B. Kephart, M. W. A. Verstegen, T. T. Canh, and P. J. Hobbs. 1999. Potential for reduction of odorous compounds in swine manure through diet manipulation. Journal of Animal Science 77:430-439.
Davis, M. E., T. Parrott, D. C. Brown, B. Z. de Rodas, Z. B. Johnson, C. V. Maxwell, T. Rehberger. 2008. Effect of a Bacillus-based direct-fed microbial feed supplement on growth performance and pen cleaning characteristics of growing-finishing pigs. Journal of Animal Science 86:1459-1467.
Acidified water—Acid-Lac Swine Poultry Data Sheet, 2011.
EcoBionics Biological System Data Sheet, believed to be published at least as early as 2016.
European Food Safety Authority Scientific Opinion on the Safety and Efficacy of Bactocell, published in the EFSA Journal 2012; 10(7):2776, Retrieved from the Internet on Feb. 16, 2015 at <URL: http://www.efsa.europa.eu/sites/default/files/scientific_output/files/main_documents/2776.pdf>.
Chedia, Aquadhi et al., Optimization of nutrient-induced germination of Bacillus sporothermodurans spores using response surface methodology, Food Microbiology, Academic Press Ltd, V. 36, N. 2, Jul. 8, 2013, pp. 320-326.
Ramirez-Peralta, Arturo et al, Effects of 1-16 sporulation conditions on the germination and germination protein levels of Bacillus subtilis spores, Applied and Environmental Microbiology Apr. 2012, V. 78, N. 8 Apr. 2012, pp. 2689-2697.
Wang Shiwei et al, Slow Leakage of Ca-Dipicolinic Acid from Individual Bacillus Spores during Initiation of Spore Germination, Journal of Bacteriology, V. 197, N. 6, Mar. 2015, pp. 1095-1103.
Luu, Stephanie et al, the Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.
Yasuda, Yoko and Tochikubo, Kunio, Relation between D-Glucose and L—and D-Alanine in the Initiation of Germination of Bacillus subtilis Spore, Microbio. Immunol. Oct. 1983, p. 197-207, vol. 28. No. 2.
Curran et al., Heat Activation Inducing Germination in the Spores of Thermotolerant and Thermophilic Aerobic Bacteria, Journal of Bacteriology; Apr. 1945; vol. 49, No. 4, pp. 335-346.
Sigmaaldrich.Com, Buffer Reference Center, Webpage [online]; Apr. 30, 2015 [date verified by web.archive.org; retrieved on Jun. 2, 2017]. Retrieved from the Internet: URL: www.sigmaaldrich.com/life-science/core-bioreagents/biological-buffers/learning-center/buffer-reference-center.
Stewart et al., Commitment of bacterial spores to germinate: A measure of the trigger reaction. Biochemical Journal. Jul. 15, 1981, vol. 198, No. 1; pp. 101-106.
Boukarim et al., Preservatives in Liquid Pharmaceutical Preparations; The Journal of Applied Research; published 2009 (month unknown); vol. 9, No. 1-2; pp. 14-17.
Nagler, et al., High Salinity Alters the Germination Behavior of Bacillus subtilis Spores with Nutrient and Nonnutrient Germinants. Applied and Environmental Microbiology. Feb. 2014, vol. 80, No. 4; pp. 1314-1321.
Busta, F.F. and Ordal, Z.J., Use of Calcium Dipicolinate for Enumeration of Total Viable Endospore Populations without Heat Activation, Applied Microbiology, Mar. 1964, p. 106-110, vol. 12, No. 2, American Society for Microbiology.

(56) References Cited

OTHER PUBLICATIONS

Carrillo-Martinez, Yarery and Setlow, Peter, Properties of Bacillus subtilis Small, Acid-Soluble Spore Proteins with Changes in the Sequence Recognized by Their Specific Protease, Journal of Bacteriology, Sep. 1994, p. 5357-5363, vol. 176, No. 17, American Society for Microbiology.

Kleijn, Roelco; Buescher, Joerg M.; Le Chat, Ludovic; Jules, Matthieu; Aymerich, Stephane; and Sauer, Uwe, Metabolic Fluxes during Strong Carbon Catabolite Repression by Malate in Bacillus subtilis, Journal of Biological Chemistry, Jan. 15, 2010, p. 1587-1596, vol. 285, No. 3, the American Society for Biochemistry and Molecular Biology, Inc.

Kong, Lingbo; Zhang, Pengfei; Wang, Guiwen; Yu, Jing; Setlow, Peter; and Li, Yong-Qing, Charactization of bacterial spore germination using phase-contrast and fluorescence microscopy, Raman spectroscopy and optical tweezers, Nature Protocols, Mar. 2011, p. 625-639, vol. 6, No. 5.

Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.

Martin, J. H. and Harper, W. J., Germination Response of Bacillus Licheniformis Spores to Amino Acids, Department of Dairy Technology, Journal of Dairy Science, Jul. 1963, p. 663-667.

Segev, Einat; Rosenberg, Alex; Mamou, Gideon; Sinai, Lior; and Ben-Yehuda, Sigal, Molecular Kinetics of Reviving Bacterial Spores, Journal of Bacteriology, May 2013, p. 1875-1882, vol. 195, No. 9.

Setlow, Peter, Summer Meeting 2013—when the sleepers wake: the germination of spores of Bacillus species, Journal of Applied Microbiology, Sep. 2013, p. 1251-1268.

Sinai, Lior; Rosenberg, Alex; Smith, Yoav; Segev, Einat; and Ben-Yehuda, Sigal, the Molecular Timeline of a Reviving Bacterial Spore, Molecular Cell, Feb. 2015, p. 695-707.

Yi, Xuan and Setlow, Peter, Studies of the Commitment Step in the Germination of Spores of Bacillus Species, Journal of Bacteriology, Jul. 2010, p. 3424-3433, vol. 192, No. 13.

Zhang, Pengfei; Setlow, Peter; and Li, Yongqing, Characterization of single heat-activated Bacillus spores using laser tweezers Raman spectroscopy, Optics Express, Sep. 2009, p. 16480-16491, vol. 17, No. 19.

Wikipedia, "Sodium chloride", Nov. 1, 2017, retrieved on Apr. 5, 2019 from https://en.wikipedia.org/w/index.php?title>Sodium_chloride&oldid>808219406, pp. 1-9.

Kemin's Acid-Lac Brand Liquid, Water Treatment for Total Gut Health, Data Sheet, believed to be published at least as early as 2011.

Gurung, Neelam, et al., a Broader View: Microbial Enzymes and Their Relevance in Industries, Medicine, and Beyond, BioMed Research International; vol. 2013, Article ID 329121.

Yazdi, Mohammed A., et al., Characterization and cloning of the gerC locus of Bacillus subtilis 168, Journal of General Microbiology, 1990, 136, 1335-1342.

Bio-Amp, Bio-Amp Biological System, Product Specifications [online] ECOBionics. [rerieved on Nov. 16, 2016]. Retrieved from the Internet: http://www.labequip.com/stock/pictures/34030.pdf.

Waites, W.M., et al., the Effect of pH, Germinants and temperature on the Germination of Spores of Clostridium bifermentans, Agricultural Research Council Food Research Institute, Journal of General Microbiology (1974), 80, 243-258.

Fortify Liquid, MSDS information available from Assist Natural Products and Services, LLC, believed to be published at least as early as 2013, Retrieved from the Internet on Feb. 16, 2015 at <URL: http://www.assist-nps.com/filesIFortify%20Liquid%20MSDS.pdf>.

Use of probiotics in aquaculture, EPA Position Paper, 2012.

Scientific opinion on the safety and efficacy of Bactocell (Pediococcus acidilactici) as a feed additive for use in water for drinking for weaned piglets, pigs for fattening, laying hens and chickens for fattening, published by the European Food Safety Authority in 2012 in the EFSA Journal 2012: 10(7):2776.

* cited by examiner

SYSTEM, METHOD, AND COMPOSITION FOR INCUBATING SPORES FOR USE IN AQUACULTURE, AGRICULTURE, WASTEWATER, AND ENVIRONMENTAL REMEDIATION APPLICATIONS

CROSS-REFERENCE TO RELATED APPLICATION

This application claims the benefit of U.S. provisional patent application No. 62/724,392 filed Aug. 29, 2018.

BACKGROUND OF THE INVENTION

1. Field of the Invention

This invention relates to use of bacteria incubated in a nutrient germinant composition and using a point-of-use spore incubation system and method comprising supplying heat produced by an exothermic chemical reaction in order to reduce organic waste, contamination, ammonia, and disease pressure and provide probiotics to species in an aquaculture, agricultural, wastewater, or environmental remediation application.

2. Description of Related Art

Aquaculture refers to the raising of aquatic species that are used as a human or animal food source. The technique typically involves rearing of aquatic species in growing ponds and applying chemicals and other treatment products to control water quality in the pond and improve the health of the aquatic species. Problems associated with this process include: pollution that is discharged from the aquaculture facility resulting in decreased water quality in the surrounding ecosystem. Loss of product due to poor water quality in the aquaculture facility; and increased disease pressures associated with pathogenic microorganisms during grow out of the stock. Such problems may be identified through testing or monitoring a variety of parameters, including but not limited to; pH, conductivity, total ammonia nitrogen, nitrite, nitrate, phosphate, and alkalinity. Conductivity is an indicator of salt content, amounts greater than 0.5 ppt is no longer considered fresh water. Ammonia measurements determine the amount of free nitrogen in a body of water. High levels of ammonia block oxygen transfer in fish from gills to the blood; however it is also a product of their metabolic waste. While ammonia from fish waste is often not concentrated enough to be toxic itself, fish and shrimp farmers must closely monitor ammonia levels due to the high density of fish per pond. Oxygen is consumed by nitrifying bacteria in the pond which break down the toxic ammonia and nitrite to a non-toxic form; however, this use of oxygen reduces the oxygen available for uptake by fish. Ammonia levels >1 ppm are considered toxic for aquacultured animals and significantly reduces overall growth and survival. Additionally, nitrate levels are examined to determine the amount of plant fertilizer in the water. Nitrate is highly leachable from the surrounding soil and can be harmful to small children and pregnant women. Alkalinity is the measure of a pond's or lake's ability to neutralize acid without a change in pH. Alkalinity will decrease over time due to bacteria. Phosphate found in ponds and lakes is largely from human and animal waste. Fertilizer run-off is a major source of phosphate found in golf course and decorative ponds. Elevated levels cause an increased rate of eutrophication which in turn increases sludge production. Moderate levels of phosphate can stimulate plant growth causing an increase in algae production; levels of >0.1 ppm is an indication of accelerated plant growth and is considered outside acceptable levels.

Agriculture refers to the intentional farming of organisms, including plants and animals, for human use or consumption. With respect to animals, the technique typically involves rearing of animal species on farms, including providing food and water to the animals, providing medications, such as antibiotics, and probiotics, to improve the health of the animals. Additionally, water quality on aquaculture farms may be improved through the use of fertilizers and chemicals. With respect to plant crops, the technique involves applying fertilizers, pesticides, and other chemicals to promote growth and inhibit diseases and pests. Problems involved with this process include, pollution that is damaging to the environment adjacent to the production facility, loss of product, decreased growth rate, discoloration of organism, harmful byproducts of raising the species produced, and increased disease pressures.

Current technologies to address these problems in aquaculture and agriculture processes include bioremediation, vaccination, antibiotics, chemical additives, and probiotic application. Typical bioremediation technologies include the application of supplemental bacteria to the water to enhance the microbiological activities to improve water quality. Nitrifiers are also used to enhance the nitrification process to convert the toxic ammonia into less-toxic nitrate. Chemical additives are also known to be added to improve the water quality and aid the microbiological activities by providing extra nutrients and alkalinity. Antibiotics are added to inhibit the growth of the pathogenic microorganisms. Problems associated with the current technologies include high cost, low nitrification activities due to the existence of organic waste and lack of substrate for bacterial growth, and bioaccumulation of antibiotics in the cultured agriculture species.

According to preferred methods disclosed in U.S. Pat. No. 9,908,799, active bacteria may be generated on-site using a biogenerator to grow the bacteria to a useful population from a solid bacteria starter material, preferably comprising spores of *Bacillus* species. The active bacteria may then be discharged into an aquaculture application from one or more biogenerators. Such biogenerators and their methods of use are disclosed, for example, in U.S. Pat. Nos. 6,335,191; 7,081,361; 7,635,587; 8,093,040; and 8,551,762, the contents of which are incorporated by reference into this disclosure. However, it would be useful to have an alternate, simplified method of generating active bacteria from spores at the point of use in an aquaculture and other applications.

In addition to treatment of water in aquaculture applications, probiotic bacteria compositions, such as those described in U.S. Patent Application Publication No. 2015/0118203 (incorporated herein by reference) and preferably comprising *Bacillus* spores, are also useful to treat animal species, plants and crops in aquaculture, farm, and agricultural applications. These probiotic compositions may be discharged to the aquaculture or agricultural application in spore form, without the spores being germinated prior to discharge. The spores will germinate when ambient conditions become favorable, which may take some time and cannot always be controlled. It would be beneficial in some circumstances to germinate the spores prior to discharge, to better control the amount of time until the bacteria become fully vegetative.

Spore germination is a multistep, causative process wherein spores effectively wake-up or are revived from a dormant state to a vegetative growth state. It is known that spores can be induced to germinate via heat-activation. Spores of various *Bacillus* species have been heat-activated at strain-specific temperatures. For example, *B. subtilis* spores have been heat-activated at 75° C. for 30 minutes while *B. licheniformis* spores have been heat-activated at 65° C. for 20 minutes. The heat-activation has been shown to cause a transient, reversible unfolding of spore coat proteins. Heat-activated spores can then be germinated for additional time in germination buffers containing nutrient germinants, such as L-alanine. If no nutrient germinant is present, however, spores will return to their pre-heated, non-germinated state.

It is also known that germination can occur at ambient temperatures (near typical room temperature) without heat-activation and with a germination buffer containing nutrients, but the process usually takes longer than with heat-activation. For example, *B. licheniformis* and *B. subtilis* spores will germinate at 35° C. or 37° C., respectively, but it takes a longer period of time (e.g. 2 hours) in a germination buffer containing nutrient germinants. Additionally, non-heat-activated spores of *B. subtilis* have been known to have been germinated in non-nutrient germinant conditions (e.g. $CaCl_2+Na_2DPA$) for an extended period of time.

It is also known to combine the use of heat activation and a nutrient germinant to germinate spores in a two-step process in laboratory settings. The spores are first heat activated by incubating for a period of time (e.g. 30 minutes) at a temperature in the range of 65-75° C. (this specific temperature is species dependent). Then, the spores are transferred into a buffer solution that contains a nutrient germinant, such as L-alanine. It is also known to grow bacteria in a growth chamber located near a use site by feeding pelletized nutrient material (containing sugar, yeast extract, and other nutrients that are not direct spore germinants), bacteria starter, and water into a growth chamber at a controlled temperature range of 16-40° C., and more preferably between 29-32° C., for a growth period of around 24 hours as disclosed in U.S. Pat. No. 7,081,361.

There is a need for a rapid spore incubation and activation method that will allow generation of active bacteria or germinated spores (that will become active bacteria after discharge to an aquaculture, agriculture, wastewater, or environmental remediation application), such as *Bacillus* species, in a single step at a point-of-use location where the bacteria will be discharged into an aquaculture or agricultural application. However, finding a heat source or providing power or gas to an electric or flame heater at a point-of-use in an aquaculture or agricultural application to heat the spores for germination may be difficult in some circumstances. Additionally, using an electric or flame heater adds to the cost and maintenance needs of an incubation system and may be difficult to use in areas exposed to the weather. There is a need for simple incubation system and method that does not require a separate electric or flame heater or a power or gas source for remote point-of-use applications. Flameless heaters comprising pouches of chemicals that exothermically react with water to provide heat are known for use in heating meals ready to eat for the military. For example, such a flameless heater is disclosed in U.S. Pat. No. 5,611,329. However, it has not previously been known to combine this flameless heater technology with a spore incubation system.

SUMMARY OF THE INVENTION

Preferred embodiments of this invention provide a simple system, method, and composition for spore germination using a nutrient germinant concentrate combined with a spore composition, or using a nutrient spore composition, simultaneously with flameless heat incubation using an exothermic chemical reaction in a cost effective single step for point-of-use discharge in aquaculture and agriculture applications that does not require an electric or flame heater. A preferred method of the invention provides a cost-effective approach to delivering an incubated bacteria solution to an aquaculture, agriculture, wastewater, or environmental remediation application to degrade organic waste and inhibit the growth of pathogenic microorganisms without bioaccumulation. An incubated bacteria solution may be supplied to animals through feed or water, to plants or crops by watering or soil application, to animal bedding or animal waste through direct application without requiring a biogenerator or an electric or flame heater. The preferred methods of the invention reduce disease pressure in the animal species in the aquaculture or agriculture application, resulting in improved harvests of the species raised in the aquaculture or agriculture operation. The preferred methods of the invention are also useful in treating wastewater.

According to one preferred embodiment of a system and method of the invention, a portable, disposable, single-use incubation container holds a flameless heater packet and a packet of nutrient spore composition. The flameless heater is activated, preferably by adding water to the disposable incubation container. Once activated, the exothermic reaction provides heat to the packet of nutrient spore composition to incubate the spores. When a desired incubation period is over, the nutrient spore composition packet is removed, opened, and an incubated bacteria solution is applied to the aquaculture, agriculture, wastewater, or environmental remediation application. The incubation container, emptied packet of nutrient spore composition, and flameless heater packet are disposed of as normal waste.

According to another preferred embodiment of a system and method of the invention, a portable, disposable, single-use incubation container holds a flameless heater packet and a mixing container, preferably a sealable mixing container. A packet of nutrient germinant composition and a separate packet of spore composition are opened and their contents emptied into the mixing container, which is then placed in the incubation container. The flameless heater is activated, preferably by adding water to the disposable incubation container. The mixing container is preferably sealed prior to placing in the incubation container and activating the flameless heater. Once activated, the exothermic reaction provides heat to the mixing container to incubate the spores. When a desired incubation period is over, the mixing container is removed, opened, and an incubated bacteria solution is applied to the aquaculture, agriculture, wastewater, or environmental remediation application. The incubation container, emptied mixing container, and flameless heater packet are disposed of as normal waste. According to another preferred embodiment, the mixing container and incubation container are the same container. According to another preferred embodiment, the spore composition and/or nutrient-germinant composition are in concentrated form and are diluted prior to activating the flameless heater by adding a diluent, such as water, to the mixing container.

U.S. application Ser. Nos. 15/479,773 and 15/907,682, which are incorporated herein by reference, disclose systems, compositions, and methods for incubating spores into a germinated spore solution or incubated bacteria solution prior to discharging to an aquaculture or agricultural application. According to one preferred embodiment of the invention, a flameless heater uses an exothermic chemical reaction to supply heat to preferred embodiments of nutrient germinant compositions and spore compositions, or combined nutrient spore compositions, in the preferred methods and using preferred systems as described in the '773 and '682 applications, to generate a germinated spore solution or an incubated bacteria solution.

Another preferred method of the invention desirably includes the delivery of an incubated bacteria solution, optionally including a probiotic bacteria, most preferably generated from an on-site incubator using a liquid nutrient germinant concentrate and bacteria in spore form that are heated by an exothermic chemical reaction in a flameless heater, into an aquaculture, agriculture, wastewater, or environmental remediation application. The incubated bacteria solution preferably include probiotic bacteria, such as one or more *Bacillus* species, and is preferably delivered into an aquaculture or agricultural application. Probiotic bacteria have been shown to change the microbial community composition in the gut of an organism to aid in digestion and improve animal health. Additionally, *Bacillus* spp. have been shown to serve as a type of nitrifying bacteria in the water column and are particularly useful in aquaculture and wastewater treatment applications. Nitrifying bacteria have the ability to reduce ammonia to nitrite, and nitrite to nitrate. Reduction of these toxic nitrogenous compounds has direct applications for the use in both aquaculture and wastewater treatment.

According to another preferred embodiment, a nutrient germinant composition also comprises spores of one or more bacteria species, preferably *Bacillus* species but other bacteria may also be used, and includes a germination inhibitor, such as NaCl, industrial preservatives, or D-alanine, in combination with any of the previously described spore composition ingredients. The germination inhibitor prevents the spores from germinating prematurely in the nutrient-germinant composition. The germination inhibitor may include chemicals that prevent spore germination such as NaCl, industrial According to another preferred embodiment, a nutrient germinant composition also comprises spores of one or more bacteria species, preferably *Bacillus* species but other bacteria may also be used, and includes a germination inhibitor, such as NaCl, industrial preservatives, or D-alanine, in combination with any of the previously described spore composition ingredients. The germination inhibitor prevents the spores from germinating prematurely in the nutrient-germinant composition. The germination inhibitor may include chemicals that prevent spore germination such as NaCl, industrial preservatives, or D-alanine.

Alternatively, bacterial spores may be separately provided and added to a nutrient-germinant composition according to the invention at the point-of-use and incubation. When separately added, it is preferred to provide a stable spore suspension spore composition comprising one or more bacteria species, preferably *Bacillus* species. According to one preferred embodiment, a spore composition comprises bacteria spores, about 0.00005 to 3.0% by weight surfactant, about 0.002 to 5.0% by weight thickener, and optionally about 0.01 to 2.0% by weight of acidifiers, acids, or salts of acids (including those used as a preservative or stabilizer), with the balance being water. According to another preferred embodiment, a spore composition comprises bacterial spores, about 0.1 to 5.0% by weight thickener, about 0.05 to 0.5% by weight acids or salts of acids, optionally about 0.1-20% by weight water activity reducers, and optionally about 0.1% to 20% additional acidifier (acids or salts of acids), with the balance being water. Preferred bacteria spore compositions include those described in U.S. Patent Application Publication No. 2015/0118203, which is incorporated herein by reference Most preferably, the bacterial spores in both preferred spore composition embodiments are in a dry, powder blend of 40-60% salt (table salt) and 60-40% bacteria spores (prior to adding to the spore composition) that combined make up about 0.1 to 10% by weight of the spore composition. The spore compositions preferably comprise around $1.0 \times 10^8$ to around $3.0 \times 10^8$ cfu/ml of the spore composition (spore suspension), which when diluted with drinking water (for animal watering applications) provide around $10^4$ to $10^6$ cfu/ml bacterial strains in the drinking water. Most preferably, the thickener in both preferred embodiments is one that also acts as a prebiotic, such as xanthan gum, to provide additional benefits. Although other commercially available spore products may be used, preferred spore compositions for use with the invention are as disclosed in U.S. application Ser. No. 14/524,858 filed on Oct. 27, 2014, which is incorporated herein by reference.

Most preferably, the bacterial spores in both preferred spore composition embodiments are in a dry, powder blend of 40-60% salt (table salt) and 60-40% bacteria spores (prior to adding to the spore composition) that combined make up about 0.1 to 10% by weight of the spore composition. The spore compositions preferably comprise around $1.0 \times 10^8$ to around $3.0 \times 10^8$ cfu/ml of the spore composition (spore suspension), which when diluted with drinking water (for animal watering applications) provide around $10^4$ to $10^6$ cfu/ml bacterial strains in the drinking water. Most preferably, the thickener in both preferred embodiments is one that also acts as a prebiotic, such as xanthan gum, to provide additional benefits. Although other commercially available spore products may be used, preferred spore compositions for use with the invention are as disclosed in U.S. application Ser. No. 14/524,858 filed on Oct. 27, 2014, which is incorporated herein by reference.

According to another preferred embodiment, a nutrient germinant composition according to the invention is in concentrated form and is diluted to 0.01% to 10% strength in water or another diluent at the point-of-use. The use of a concentrated formula reduces shipping, storage, and packaging costs and makes dosing of the spore composition at the point-of-use easier. Most preferably, the concentrated spore composition is in a liquid form, which is easier and faster to mix with diluent at the point-of-use, but solid forms such as pellets or bricks or powder may also be used. The inclusion of a general, industrial preservative in the spore composition aids in long-term storage and/or germination inhibition, which is particularly useful when the spore composition is in the preferred concentrated form.

In another preferred embodiment, the present invention comprises a method of germinating spores of *Bacillus* species using a nutrient germinant composition combined with a spore composition or using a nutrient spore composition at an elevated temperature; preferably in a range of 35-60° C., more preferably in the range of 38-60° C. or 38-50° C., and most preferably in the range of 41° C. to 44° C. for a period of time (an incubation period). The incubation period preferably ranges from 2-60 minutes, or longer, depending on the application. Most preferably, a nutrient-germinant composition or nutrient spore composition in concentrated form according to preferred embodiments of the invention are used in the incubation/germination methods of the invention, but other nutrient-germinant compositions and spore compositions may also be used. Preferably, the incubation method is carried out at or near the point-ofuse—the aquaculture, agriculture wastewater, or environmental remediation site where the incubated spores will be used or consumed and further comprises dispensing the germinated spores to the point-of-use/consumption. Preferred methods according to the invention may be carried out in any incubation device that has a container, reservoir, or tank capable of holding a volume of spores (if separately added), liquid (typically water as a diluent), and a nutrient-germinant composition and that is capable of disposing a flameless heater, such as that disclosed in U.S. Pat. No. 5,611,329, in close proximity to the spores and nutrient-germinant composition to heat them to within the desired incubation temperature ranges during an incubation period. Most preferably, the methods are carried out in a device that is also capable of mixing those ingredients and automatically dispensing an incubated bacteria solution comprising the bacteria to an aquaculture, agriculture, wastewater, or environmental remediation point-of-use/consumption, although the incubated solution may also be manually discharged to the point-of-use/consumption. Preferred methods may also be carried out as a batch process or as a continuous process. Although spore compositions according to the invention are preferably used, any variety of spore forms or products, such as dried powder form, a liquid suspension, or a reconstituted aqueous mixture, may be used with the method of the invention.

An incubated bacteria solution includes bacteria that are primarily still spore form bacteria, primarily metastable state bacteria (in which the spores are neither dormant nor in the vegetative growth phase, also referred to herein as an activated state), or primarily fully vegetative bacteria, depending on the species of bacteria used, incubation temperature, incubation time, and content of the nutrients used. A nutrient-germinant composition according to one preferred embodiment of the invention comprises one or a combination of many L-amino acids, optionally D-glucose (which increases the binding affinity of L-amino acids for their cognate receptors in the spore coat), and a neutral buffer such as a phosphate buffer, and an industrial preservative, such as the commercially available Kathon/Lingaurd CG (which has active ingredients comprising methyl chloro isothiazolinone and methyl isothiazolinone). A nutrient-germinant composition according to another preferred embodiment of the invention comprises one or a combination of two or more L-amino acids, optionally D-glucose (which increases the binding affinity of L-amino acids for their cognate receptors in the spore coat), HEPES sodium salt (a biological buffer to provide the proper pH for spore germination), and an industrial preservative, such as a combination of propylparaben and methylparaben or other U.S. federal GRAS (Generally Regarded As Safe) preservatives. According to another preferred embodiment, the spore composition also comprises a source of potassium ions, such as potassium chloride or monopotassium phosphate or dipotassium phosphate. According to another preferred embodiment, the spore composition includes both D-glucose and D-fructose.

The preferred embodiments of the invention allow for rapid incubation or germination of spores of *Bacillus* species at an aquaculture, agriculture, wastewater, or environmental remediation point-of-use without requiring any electric or flame heater. Preferred embodiments of systems of the invention are easily accessible, easily stored, and compact, and the use of a nitrifying aid will allow for cost-effective treatment of agriculture and aquaculture applications, including treatment for ammonia, as well as, general water quality issues and to provide probiotic benefits to animals and aquatic species that ingest the bacteria. The incubated bacteria solution discharged from the incubator can be supplied directly to growing ponds, animal feed or drinking water, plants, or crops, wastewater systems, or environmental remediation site, or can be accumulated and diluted with pond water or another similarly suitable diluent, such as water from a municipal water system, prior to discharging it into growing ponds, animal feed or drinking water, plants, or crops, wastewater systems, or environmental remediation site. Preferably, the spores are incubated at a temperature and for an incubation period to achieve the desired type of incubated bacteria solution, which may be primarily still spore form bacteria, primarily metastable state bacteria (in which the spores are neither dormant nor in the vegetative growth phase, also referred to herein as an activated state), or primarily fully vegetative bacteria. If discharged as spores or metastable state bacteria, the bacteria will preferably go on to develop into active, fully vegetative bacteria in the point of use application. If discharged as spores or metastable state bacteria, the bacteria will preferably go on to develop into active, fully vegetative bacteria in the point of use application. Dilution may aid in delivery of the treatment solution flowing from the incubator to the aquaculture, agriculture, wastewater, or environmental remediation application, if the incubator is located some distance from the application. The active bacteria will degrade the organic waste and inhibit the growth of the pathogenic microorganisms in the water in the aquaculture, agriculture, and wastewater facilities, without requiring the addition of (or reducing the amount of) chemical treatments and antibiotics used in the applications. The bacteria may also serve as probiotics for plant and animal species.

Preferred embodiments of the system, method and composition may be used in various types of aquaculture applications, including hatcheries, ponds, and tidal flow aquaculture; agricultural applications, including animal water sources for hatcheries and livestock grow-out stages and plant and crop watering applications during all stages of crop production. Although primarily described herein with respect to aquaculture and agriculture application, the system, method and composition of preferred embodiments of the invention are also useful in water treatment applications in wastewater and industrial facilities and for environmental remediation applications, such as land (soil) or water systems that have been contaminated.

BRIEF DESCRIPTION OF THE DRAWINGS

The system and method of the invention are further described and explained in relation to the following drawings

DESCRIPTION OF THE PREFERRED EMBODIMENTS

Aquaculture, Agriculture, and Wastewater Treatment Methods

According to one preferred embodiment, an incubated bacteria solution is generated on site from a nutrient germinant composition combined with a spore composition or from a premixed nutrient spore composition, preferably using an incubator system and a preferred germination method as described below, and the active bacteria are fed into a growing pond in an aquaculture application or fed to animals or applied to crops in an agriculture application or a wastewater system. An incubated bacteria solution may be periodically generated and supplied to the aquaculture, agriculture, wastewater, or environmental remediation application in an automated or semi-automated system or may be manually supplied on an as-needed basis. For an aquaculture application, it is preferred that the incubated bacteria solution comprise primarily activated, vegetative bacteria. One or more nitrification enhancement agents are also preferably contemporaneously added (at or near the time the incubated bacteria solution is added) to the growing pond with the incubated bacteria solution in an aquaculture application.

Figure 1:
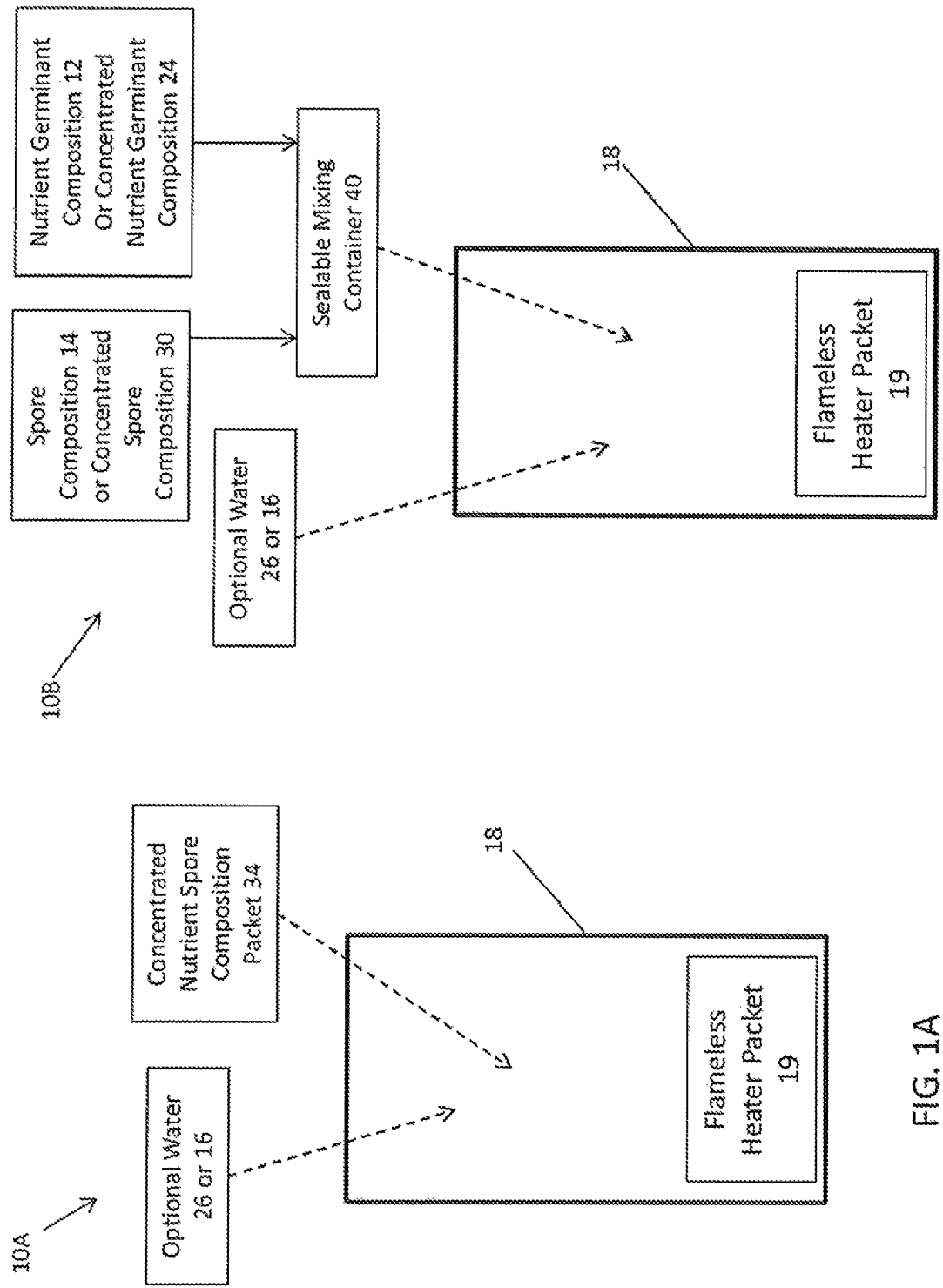
FIG. 1A is a diagram for a portable incubation system and method according to a preferred embodiment of the invention.
FIG. 1B is a diagram for a portable incubation system and method according to another preferred embodiment of the invention.
Figure 2:
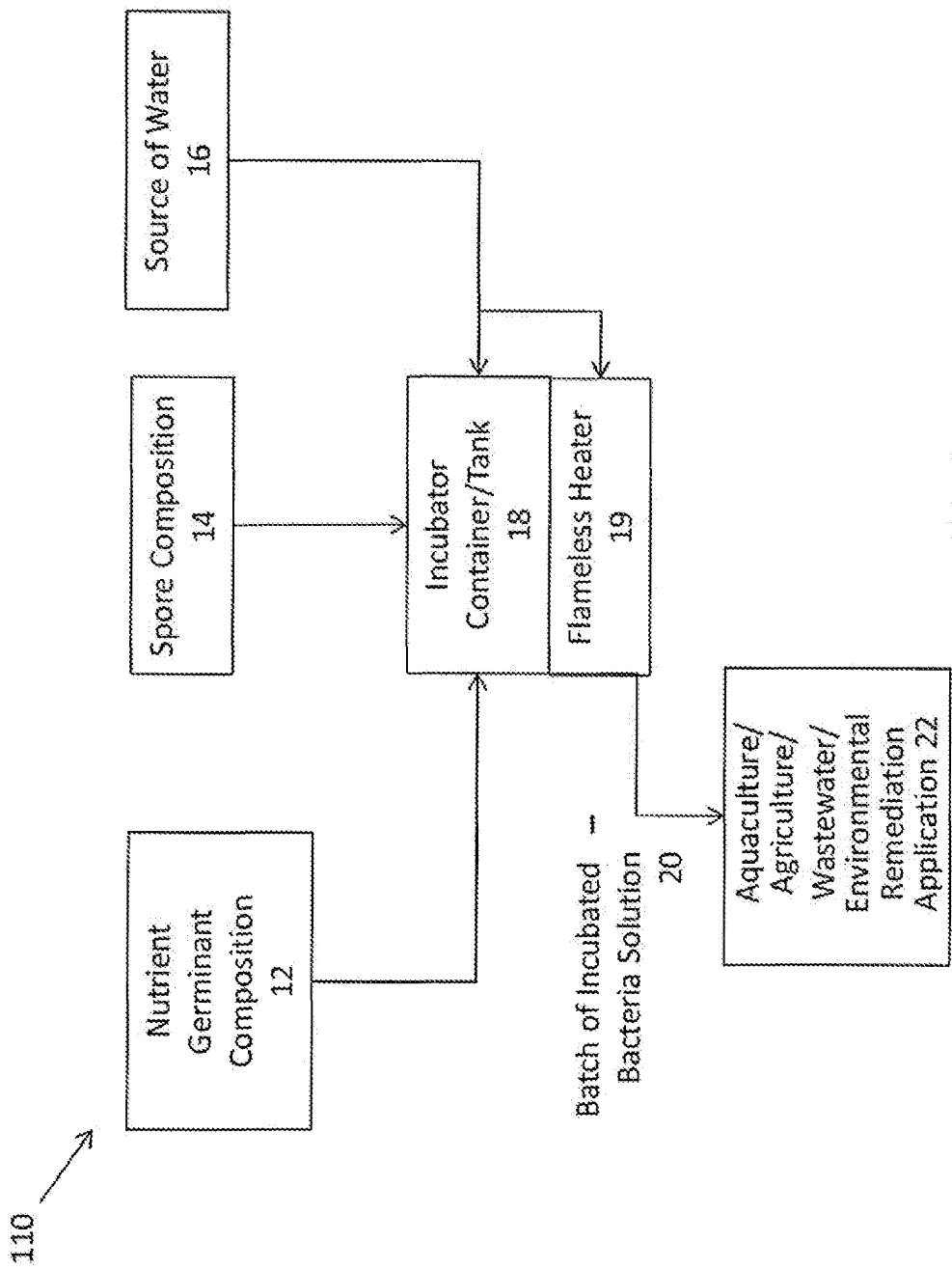
FIG. 2 is a flow diagram for an incubation system and method according to a preferred embodiment of the invention.
Figure 3:
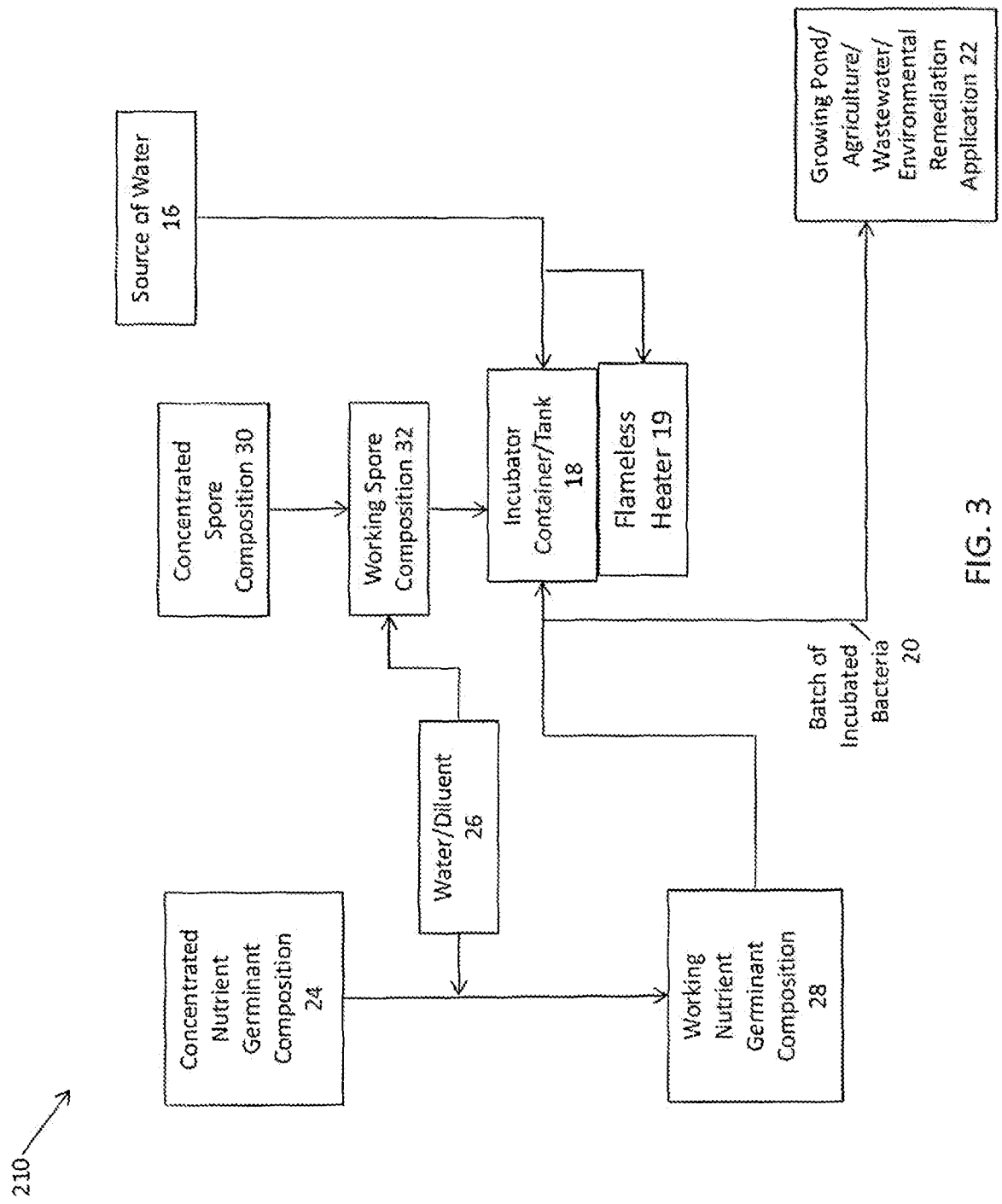
FIG. 3 is a flow diagram for an incubation system and method according to another preferred embodiment of the invention.
Figure 4:
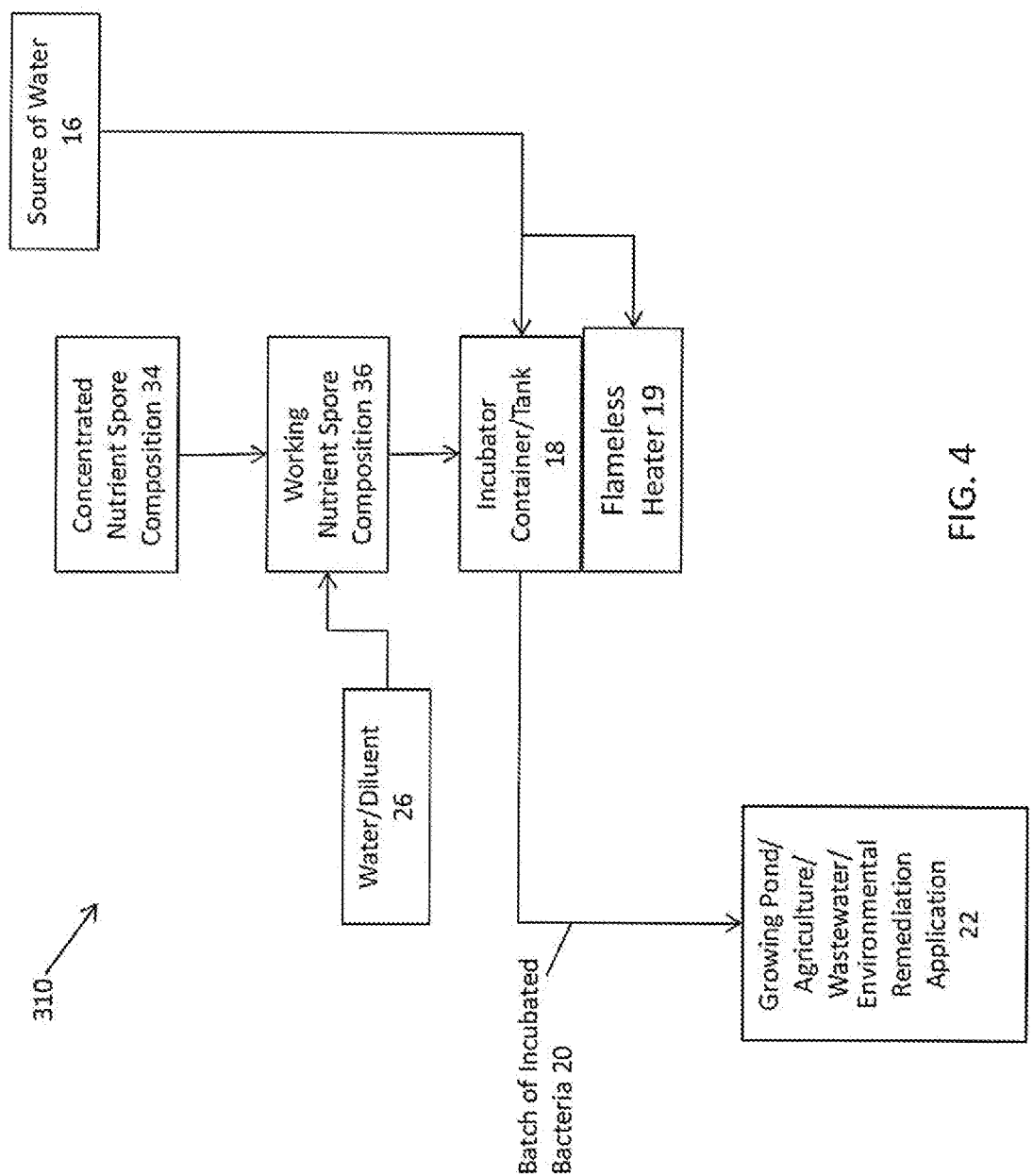
FIG. 4 is a flow diagram for an incubation system and method according to another preferred embodiment of the invention.

A preferred embodiment of an on-site, portable incubator system 10A comprises one or more containers for holding a nutrient-germinant composition and a spore composition that are mixed together to form a nutrient-spore composition or for holding a pre-mixed nutrient spore composition and a non-electric, non-battery, and non-gas powered heater. Preferably, as shown in FIG. 1A, system 10A comprises a container or small packet holding an amount of a concentrated nutrient spore composition 34, a larger incubation container 18, and a flameless heater packet 19. Packet 34 preferably comprises a nutrient spore composition according to preferred embodiments of such composition described below. Most preferably, packet 34 is made from non-porous material that is non-permeable to gas and water. Incubation container 18 preferably comprises a transparent or clear plastic bag of sufficient size to hold the packet of nutrient spore composition 34, flameless heater packet 19, and an optional (but preferred) amount of water 16 supplied at the point of use. Other types of containers may also be used. Container 18 preferably includes markings for a fill-line, indicating how much water should be added to container 18 to activate flameless heater 19 and/or to provide some diluent to the nutrient spore composition. Alternatively, container 18 may include instructions for a quantity of water (such as two cups) to be added to the container. Preferably container 18 is sealable so that it need not be manually held closed by a user during heating. As an alternative, container 18 may also be divided, with one side to contain the flameless heater and any activation water added and another side to contain the nutrient spore composition packet 34. A well at or near the point of use, a municipal water supply, bottled water, or a growing pond may provide water 16 that may be added to container 18.

Incubator system 10 also preferably comprises a flameless heater 19, such as that disclosed in U.S. Pat. No. 5,611,329, although other exothermic chemical reaction heaters may also be used for flameless heater 19. Flameless heater 19 preferably comprises a pouch filled with a powdered mixture of chemical(s) that react exothermically in the presence of another chemical, water, or air. One preferred flameless heater 19 comprises a water and gas permeable plastic pouch filled with a magnesium 5 atomic weight iron supercorroding alloy, an inert filler, sodium chloride, and antifoaming agents, such as that described in U.S. Pat. No. 5,611,329, which is incorporated herein by reference. Another preferred flameless heater 19 comprises chemicals in an inner pouch disposed within an outer air permeable pouch that will react with air when the inner pouch is broken, such as the type typically used for hand warmers. Another preferred flameless heater 19 comprises a divided pouch or an inner pouch disposed within an outer pouch. A first chemical is disposed within one portion of the divided pouch or within the inner portion, and a second chemical (or water or air) that will react with the first chemical in an exothermic reaction is disposed in the other portion of the divided pouch or within the outer pouch. The inner pouch or the divider between the pouches is then broken to allow the first and second chemicals to contact each other, begin reacting, and provide heat to incubator tank 18.

When it is desired to generate an incubated bacteria solution, flameless heater 19 is preferably placed inside container 18 and a packet of concentrated nutrient spore composition 34 is also placed inside container 18. Container 18 may also be sold with heater 19 and packet 34 already inside, sold as a single unit containing the primary components needed to generate an incubated bacteria solution. If flameless heater 19 is activated by water, then water is added to container 18, preferably to a level as indicated on container 18 or in a desired amount and the chemical reaction will begin and will provide sufficient heat to the nutrient spore composition packet 34 to initiate germination of the bacteria spores. If not activated by water, then the user preferably breaks the inner pouch or the divider between pouches to initiate the chemical reaction or opens the previously sealed container 18 to allow air inside.

After a desired incubation period, preferably in accordance with preferred incubation methods described below, the packet 34 (now containing an incubated bacteria solution 20) is removed from container 18, and incubated bacteria solution 20 is manually supplied to the desired aquaculture, agriculture, wastewater, or environmental remediation application by opening the packet and pouring its contents onto the aquaculture, agriculture, wastewater, or environmental remediation application. Since packet 34 is a concentrated composition, it is preferred to add incubated bacteria solution to a water source, such as animal drinking water or crop watering source, in an agriculture application to aid in dispersal of the solution.

Another preferred embodiment of an on-site, portable incubator system 10B, comprises one or more containers for holding a nutrient-germinant composition and a spore composition that are mixed together to form a nutrient-spore composition or for holding a pre-mixed nutrient spore composition and a non-electric, non-battery, and non-gas powered heater. Preferably, as shown in FIG. 1B, system 10B comprises a container or small packet holding an amount of a nutrient germinant composition 12 or concentrated nutrient germinant composition 24, a container or small packet of bacteria spore solution 14 or concentrated bacteria spore solution 30, a sealable mixing container 40, a larger incubation container 18, and a flameless heater packet 19. Packets 12, 24, 14, and 30 preferably comprise compositions according to preferred embodiments of such compositions described below. Most preferably, packets 12, 24, 14, and 30 and container 40 are made from non-porous material that is non-permeable to gas and water. Container 18 and flameless heater 19 in system 10B are the same as described with respect to system 10A. Generation of an incubated bacteria solution and its application are the same in system 10B as in system 10A except that, because the nutrient germinant and spores are in separate packets, the contents of packets 12/24 and 14/30 must be emptied into a mixing container 40 (preferably a sealable mixing container) prior to placing container 40 inside incubation container 18 for heating so that the nutrient germinant and spores can mix together during heating. Alternatively, a mixing container and incubation container may be the same container such that incubation container 18 serves as the mixing container when the contents of packets 12/24 and 14/30 are added or emptied directly into container 18, along with optional water, and heated in the same container. Most preferably, if incubation container 18 serves as the mixing container, it is a divided container to segregate the mixed nutrient spore composition from the flameless heater or the contents of the flameless heater 19 are sealed and are not allowed to mix with the nutrient spore composition.

Once the incubation period is complete, the contents of container 18 (except the flameless heater packet 19) are supplied to the aquaculture, agriculture, and wastewater application. Since the chemical reaction in flameless heater packet 18 may produce reaction byproducts that may be undesirable for use in a particular aquaculture, agriculture, and wastewater applications, it is preferred to either use a (1) a divided container 18, having one side for the flameless heater and a separate side for the contents of the packets 34 or 12/24 and 14/30, that allows heat to transfer to the bacteria side without allowing contact with any byproducts or (2) use a sealed packet 34 or a sealed mixing container 40 to protect the incubated bacteria solution from contact with such byproducts. Once the incubation period is over, container 18, flameless heater 19, and any water contents or byproducts in container 18 may be discarded as normal waste.

Although it is preferred to use a nutrient germinant composition to enhance incubation, a bacteria spore solution 14/30 may be used with systems 10A or 10B alone to heat treat the spores prior to application to an aquaculture, agriculture, wastewater, or environmental remediation application. Heat treating the spores will aid in germination; however, the results are improved when a nutrient germinant composition according to preferred embodiments of the invention is also used.

Preferably, flameless heater 19 heats to within the desired incubation temperatures according to preferred embodiments of the incubation method described below. Commercially available flameless heaters are known to heat to around 38° C. (100 F) after around 15 minutes of reaction time. Typically, flameless heater 19 will produce sufficient heat and retain heat for up to 30 minutes that one packet is sufficient for a desired incubation period. However, if a longer incubation period is desired, one or more additional flameless heater packets 19 may be added to container 18 after or during the reaction of the previous packet. Additionally, any of the packets 34, 12/24, or 14/30 that are added to container 18 may be made of insulating materials, if it is desired to reduce the temperature exposure of the contents of the packets from the maximum temperature that will be reacted in the exothermic chemical reaction in flameless heater 19.

Systems 10A/10B are preferably simple, portable and manually operated systems, where a pouch or container of nutrient-germinant composition and a pouch or container of spore composition (if not already premixed with the nutrient-germinant composition) are manually added to container 18 along with a flameless heater packet 19, water is manually added to tank 18 as needed to dilute the compositions and/or initiated the chemical reaction in flameless heater 19, the compositions are optionally manually mixed, and the flameless heater 19 reaction is manually triggered by adding water or breaking the pouch of chemical(s). Once the incubation period is over, the incubated bacteria solution 20 is manually discharged to the desired aquaculture, agriculture, or wastewater application 22. This allows for a very simple system and method of generating an incubated bacteria solution at a point-of-use and supplying that solution to an aquaculture, agriculture, wastewater, or environmental remediation application, without requiring any power or an electric or flame heater. Systems 10A and 10B are preferably used for emergency treatment or sporadic treatment of an aquaculture, agriculture, wastewater, or environmental remediation application, whereas other preferred systems of the invention as described herein are preferably used for on-going treatments. Container 18, the packets for the nutrient and spore compositions, and flameless heater packet 19 may be disposed of as normal waste once the incubated bacteria solution is applied. Systems 10A and 10B are preferably lightweight, preferably weighing less than 5 lbs. to make them easy to carry to a point of use.

Other preferred embodiments of on-site incubator systems 110, 210, and 310 are shown in FIG. 2-4. Systems 110, 210, and 310 are also simple, manually operated systems, similar to systems 10A/10B, but with more permanent or reusable components, such as tank 18 and optionally plumbing to supply water from water source 16. System 110 preferably comprises one or more tanks or holding containers for holding an initial volume of nutrient germinant composition 12 and an initial volume of bacteria spore solution 14 (if the bacterial spores are not included in the nutrient germinant composition) and an incubator tank, reservoir, or other type of container 18 configured to receive at least a portion of the nutrient germinant composition 12 and spore solution 14 (if not already premixed with the nutrient germinant composition). These spore and nutrient germinant compositions may also arrive at the site of use in containers that are connectable in fluid communication with incubator 18, in which case separate tanks or containers are not needed. A source of water 16 at or near the aquaculture, agriculture, wastewater, or environmental remediation site is also optionally, but preferably, connectable in fluid communication with the incubator system. A well, source of municipal water supply, or the growing pond may provide water 16 to the incubator container or reservoir 18.

An incubator system 110 also preferably comprises a flameless heater 19, as previously described with systems 10A/10B. Flameless heater 19 is preferably disposed in close proximity to incubator tank 18 to supply heat to the incubator tank 19 when a portion of the nutrient-germinant composition and spore composition have been added to the incubator tank 18. Flameless heater 19 preferably comprises a pouch filled with a powdered mixture of chemical(s) that react exothermically in the presence of another chemical, water, or air. One preferred flameless heater 19 comprises a water and gas permeable plastic pouch filled with a magnesium 5 atomic weight iron supercorroding alloy, an inert filler, sodium chloride, and antifoaming agents, such as that described in U.S. Pat. No. 5,611,329, which is incorporated herein by reference. Another preferred flameless heater 19 comprises chemicals in an inner pouch disposed within an outer air permeable pouch that will react with air when the inner pouch is broken, such as the type typically used for hand warmers. Another preferred flameless heater 19 comprises a divided pouch or an inner pouch disposed within an outer pouch. A first chemical is disposed within one portion of the divided pouch or within the inner portion, and a second chemical (or water or air) that will react with the first chemical in an exothermic reaction is disposed in the other portion of the divided pouch or within the outer pouch. The inner pouch or the divider between the pouches is then broken to allow the first and second chemicals to contact each other, begin reacting, and provide heat to incubator tank 18. Flameless heater 19 is preferably disposed under tank 18, but may also be disposed around one or more sides of tank 18 or within tank 18. Water from water source 16 may be supplied to flameless heater 19 to initiate the exothermic reaction if water is the reactant for the chemical within the pouch. Flameless heater 19 may also be disposed inside a container or tank to hold water in contact with the pouch of chemical(s) when water is used as the reactant.

Preferably, flameless heater 19 heats to within the desired incubation temperatures according to preferred embodiments of the incubation method described below. Commercially available flameless heaters are known to heat to around 38° C. (100 F) after around 15 minutes of reaction time. Typically, flameless heater 19 will produce sufficient heat and retain heat for up to 30 minutes that one packet is sufficient for a desired incubation period. However, if a longer incubation period is desired, one or more additional flameless heaters 19 may be used by initiated the chemical reaction in a new flameless heater 19 after or during the reaction of the previous heater. Additionally, incubator 18 and/or a container for flameless heater 19 may be made of insulating materials, if it is desired to reduce the temperature exposure of the contents of incubator 18 from the maximum temperature that will be reacted in the exothermic chemical reaction in flameless heater 19.

As with system 10A/10B, system 110 is preferably manually operated. A pouch or container of nutrient-germinant composition and a pouch or container of spore composition (if not already premixed with the nutrient-germinant composition), or a portion of an initial, larger volume of these compositions, are manually added to tank 18, water is manually added to tank 18 as needed to dilute the compositions (and/or to initiated the chemical reaction in flameless heater 19 if it is disposed within tank 18), the compositions are manually mixed, and the flameless heater 19 reaction is manually triggered by adding water to a separate container for the heater (if not disposed within tank 18) or breaking the pouch of chemical(s). Although a single flameless heater 19 packet is preferably sufficient, additional packets may be manually added and the reaction triggered as needed to maintain the temperature within the desired range over a desired incubation period. Once the incubation period is over, the incubated bacteria solution 20 is discharged to the desired aquaculture, agriculture, wastewater, or environmental remediation application 22. System 110 preferably includes one or more manually activated valves and tubing connected to tank 18 and/or a separate container for flameless heater 19, to aid in adding the compositions and water to the tank 18, adding water to the flameless heater 19 as needed, and discharging the incubated bacteria solution 20 from tank 18, all preferably by gravity flow or by pressure supplied in a municipal water supply. This allows for a very simple system and method of generating an incubated bacteria solution at a point-of-use and supplying that solution to an aquaculture, agriculture, wastewater, or environmental remediation application, without requiring any power or an electric or flame heater.

Other features of system 110 may also be automated, including valves and pumps (as needed, if gravity flow is not sufficient) to allow the nutrient germinant composition 12, bacteria spore solution 14, and optionally water 16 to flow from their storage containers/source into incubator tank 18 and to discharge an incubated bacteria (or activated bacteria) solution 20 from tank 18 and deliver it to the aquaculture, agriculture, wastewater, or environmental remediation application 22; an optional mixer within the incubator tank 18, and a controller or timer to activate the valves, pumps, optional mixer, to control influx of the nutrient and spore compositions into the incubation tank 18, addition of water to flameless heater 19, incubation time and discharge to the aquaculture, agriculture, wastewater, or environmental remediation application 22. In either manual or automated forms, or a combination thereof, on-site incubator system 110 preferably uses a nutrient germinate composition combined with a bacteria spore composition (as described below) or uses a nutrient spore composition (a nutrient germinant composition pre-mixed with bacteria spores, also as described below) (either are also referred to herein as "starter material"), to generate an incubated bacteria solution 20 to be discharged into the aquaculture, agriculture, wastewater, or environmental remediation application 22.

Alternatively, according to another preferred embodiment as shown in FIG. 3, incubator system 210 uses concentrated nutrient germinant composition 24 and concentrated spore composition 30, which are diluted with a diluent or water from container/source 26 to form a working nutrient germinant composition 28 and a working spore composition 32, a portion of each being fed into incubator 18 to generate a batch of activated bacteria 20. Water from source 16 may also be used as a source of diluent in place of or in addition to source 26. Additionally, only one of the nutrient germinant composition 24 or spore composition 30 may be in concentrated form and require dilution prior to feeding into incubator 18. According to another preferred embodiment, when only one is concentrated, the non-concentrated composition may be used as a diluent for the concentrated composition in addition to or in place of water/diluent from source 26 and/or source 16. According to another preferred embodiment, a concentrated nutrient spore composition 34 is used with system 310 as shown in FIG. 4. The concentrated nutrient spore composition is diluted with water/diluent from source 26 and/or source 16 to make a working nutrient spore composition 36 prior to feeding into incubator 18 to generate a batch of activated bacteria 20. Alternatively, a nutrient spore composition may not be in concentrated form and not require any diluent prior to feeding into incubator 18 (similar to direct feeding of nutrient germinant composition 12 in FIG. 2), in which case water/diluent source 26 is not needed. Water from source 16 may still be optionally fed into incubator 18 as needed in this alternate embodiment. With any of the incubator system embodiments, diluent may be fed into incubator 18 to dilute a concentrated composition within the incubator rather than prior to feeding the incubator. Any combination of elements from systems 10A/10B, 110, 210, and 310 may be used together, as will be understood by those of ordinary skill in the art.

Preferably, bacteria spores are germinated in incubator container or tank 18 according to preferred germination methods described herein. Commercially available flameless heaters are generally able to heat to a temperature of around 38° C. (100 F) above starting temperature (or ambient temperature) in around 12-15 minutes. According to one preferred embodiment, a nutrient germinant composition and spore composition (or nutrient spore composition) are heated in container or incubator 18 using flameless heater 19 to a temperature of around 35° C. to around 90° C., more preferably around 38° C. to around 90° C. The incubation temperature may be any individual temperature or sub-range within the range of 35° C. to around 90° C. According to another preferred embodiment, the composition(s) are heated to a temperature in a range of 35-55° C., more preferably in the range of 38-50° C. or 38-60° C., and most preferably in the range of 41° C. to 44° C. The incubation period can vary depending on the end-use application and particular flameless heater 19 used, but is preferably between 2-60 minutes, more preferably between around 10-15 minutes. To generate active bacteria for an aquaculture, agriculture, wastewater, or environmental remediation application, a preferred incubation period is around 20 minutes to 60 minutes and for a probiotic application to generate metastable state bacteria is preferably around 2 minutes to 5 minutes. To provide additional growth time for vegetative bacteria, the incubation period may be around 4 to 6 hours. Packet 34 or mixing container 40 may be removed from container 18 prior to the end of the chemical reaction in systems 10A/10B, if desired. Similarly, the contents of incubator 18 may be discharged prior to the end of the chemical reaction in systems 110, 210, or 310, if desired.

Depending on the desired use of the bacteria in the aquaculture, agriculture, wastewater, or environmental remediation application, such as use to treat the water or a probiotic for the aquatic species, different incubation periods may be used to provide an incubated bacteria solution that is primarily still spore form bacteria, primarily metastable state bacteria (in which the spores are neither dormant nor in the vegetative growth phase, also referred to herein as an activated state), or primarily fully vegetative bacteria. Additionally, when fully vegetative bacteria are desired, the bacteria solution may be held within the incubator tank 18 or another intermediate container for a period of time after the incubation period to allow the bacteria to multiply prior to discharging into the aquaculture, agriculture, wastewater, or environmental remediation application. Most preferably, the bacteria solution will be maintained at a temperature between 30 to 45° C., more preferably, the vegetative bacteria solution will be heated as necessary to maintain the temperature of the solution in the range of 33 to 42° C., and most preferably in the range of 36° C. to 39° C. to facilitate growth during this post incubation growth period. When a probiotic application is desired, the bacteria remain primarily in the spore state or metastable state when discharged to the aquaculture application by using a shorter incubation period, which gives the bacteria a better chance of surviving through to the aquatic species' intestinal tract where they are most beneficial as probiotics. At the end of an incubation period, an incubated bacteria solution 20 is discharged to the aquaculture, agriculture, wastewater, or environmental remediation application. An incubated bacteria solution 20 may comprise fully vegetative bacteria, metastable state bacteria, spores, or a combination thereof depending on the species of bacteria used, incubation temperature, incubation time, and content of the nutrients used.

Pouches of chemicals in flameless heater 19 may be replaced as needed with new pouches to maintain temperatures within the desired ranges during an incubation period and/or during a post incubation growth period.

Each batch of incubated bacteria solution 20 comprises around $1 \times 10^8$-$1 \times 10^{10}$ cfu/mL of metastable state, vegetative bacteria species, and/or spores. In aquaculture, agriculture, and wastewater applications into once discharged into an applicable water source 22 (such as a growing pond or wastewater tank), the amount of bacteria in each batch is diluted based on the amount of water in the water source. Most preferably, sufficient quantities of bacteria solution 20 are added to the applicable water source 22 to provide an effective amount of activated bacteria based on the dilution in the growing pond, drinking water, wastewater tank or system, or other water container. In this context, "effective amount" can refer to the amount of bacteria and/or nutrient composition that can be effective to improve performance of a plant or animal after administration or improve wastewater conditions. An improvement in performance can be measured or evaluated by monitoring one or more characteristics, including but not limited to water quality: clarity of water, ammonia levels, nitrite levels, nitrate levels, disease incidence, mortality, harvest weight, meat quality, individual animal size, premium weights, antibiotic use, and additive use. "Effective amount" can also refer to the amount that can reduce the amount of, competitively exclude, and/or eliminate one or more species of pathogenic bacteria (including, but not limited to *Escherichia coli* and *Salmonella*) in the intestines of an animal. "Effective amount" can also refer to the amount that can reduce $NH_3$, such as that which can be excreted by an animal into its environment, and/or $H_2S$ levels, which may be an issue in wastewater applications.

According to one preferred embodiment for use in contained aquaculture applications, the effective amount of the bacteria in the growing pond can be about 1 to about $9 \times 10^2$ CFU/mL. According to another preferred embodiment, the effective amount for contained aquaculture applications is about 1 to about $9 \times 10^2$ to about $10^8$ CFU/mL. According to another preferred embodiment, the effective amount of the incubated bacteria in the growing pond can range from about 0.001% to about 2% v/v of the total amount of water in the growing pond and any range or value therein. As another example, around 500 mL of incubated bacteria solution comprising around $1 \times 10^9$-$1 \times 10^{10}$ cfu/mL of bacteria species dosed to a growing pond four times per day will be sufficient treat a growing pond containing 100,000 gallons of water. Other volumes of bacteria solution and dosing intervals may be used to treat growing ponds, depending on the size of the pond, based on pond conditions, aquatic species, temperature of the pond, and other factors to achieve a desired effective amount of bacteria in the pond as will be understood by those of ordinary skill in the art.

Multiple incubator systems 110, 210, or 310 may be provided to provide larger quantities of incubated bacteria solution to the aquaculture, agriculture, wastewater, or environmental remediation application achieve the desired effective amount being added to the application, to provide different species of bacteria to the application or at different times or rates, and/or to space out the discharge of incubated bacteria solution around the perimeter of a water source in the application (such as a growing pond, to aid in dispersing the bacteria through the pond). A pump or other mixing device may also be added to a growing pond or other water source (if not already in place) to aid in dispersing the incubated bacteria solution (and nitrification enhancers or surface area enhancers, if used) throughout the growing pond or water source.

Portable, on-site incubators 10A/10B are preferably configured to generate a single batch of incubated bacteria solution for each container 18 and flameless heater 19. Multiple batches may be generated as needed by using multiple systems 10A or 10B, with container 18 and flameless heater 19 being discarded after a single use.

On-site incubator systems 110, 210, and 310 are preferably configured to incubate multiple batches of incubated bacteria solution from a larger container of a nutrient germinant composition/spore composition or nutrient spore composition than would be used with systems 10A/10B, so that multiple batches of bacteria can be discharged at periodic intervals over a prolonged period of time before the starter material needs to be replenished. The volume of nutrient germinant composition/spore composition or nutrient spore composition feeding the incubator is periodically replaced or replenished as needed. A treatment cycle is preferably continuous with the incubator running throughout the year (other than periodic shut-downs for maintenance or replenishment of the nutrient germinant composition).

In systems 110, 210, or 310, an incubated bacteria solution 20 is preferably discharged from one or more incubators 18 to the aquaculture, agriculture, wastewater, or environmental remediation application 22 once every 4 to 6 hours over the course of a treatment cycle. In systems 10A/10B a single dose of incubated bacteria solution 20 is preferably supplied to the aquaculture, agriculture, wastewater, or environmental remediation application with every disposable container 18 used. Multiple doses may be manually provided by using multiple systems 10A/10B at desired intervals, such as every 4 to 6 hours, over a treatment cycle. Other dosing intervals for systems and methods according to the invention may be used depending on the size of aquaculture, agriculture, wastewater, or environmental remediation application, conditions of the pond/aquatic or animal species, and type of species or animals. The time between doses may be varied as desired by varying the timing of addition of ingredients to the incubator and/or incubation time. An incubated bacterial solution may be discharged more frequently on a larger pond (e.g. 20 million gallons) or larger agriculture, wastewater systems, or environmental remediation site applications. For an aquaculture wastewater, or environmental remediation treatment application, it is preferred to discharge an incubated solution having vegetative bacteria. To achieve vegetative bacteria, it is preferred to incubate for at least 4 to 6 hours before discharging to the growing pond, although longer incubation times to allow more time for the bacteria to multiply may also be used. For a probiotic application for aquatic or agricultural species, it is preferred to incubate for around 2 to 5 minutes. In that application, an incubated bacteria solution 20 may be discharged multiple times a day, even as frequently as every 4 to 6 minutes, if needed for a large pond or agriculture facility.

Various *Bacillus* species, as described below, are preferably used with aquaculture treatment methods according to the invention, but other bacteria may also be used. For example, the genera of bacteria suitable for use in the method of the invention are believed to include any one or more species in the genera *Bacillus, Bacteroides, Bifidobacterium, Lueconostoc, Pediococcus, Enterococcus, Lactobacillus, Megasphaera, Pseudomonas* and *Propionibacterium*. Probiotic bacteria that may be generated on-site include any one or more of the following: *Bacillus amylophilus, Bacillus licheniformis, Bacillus pumilus, Bacillus subtilis, Bacillus amyloliquefaciens, Bacillus coagulans, Bacillus megaterium, Bacteroides ruminocola, Bacteroides ruminocola, Bacterioides suis, Bifidobacterium adolescentis, Bifidobacterium animalis, Bifidobacterium bifidum, Bifidobacterium infantis, Bifidobacterium longum, Bifidobacterium thermophilum, Enterococcus cremoris, Enterococcus diacetylactis, Enterococcus faecium, Enterococcus intermedius, Enterococcus lactis, Enterococcus thermophiles, Lactobacillus brevis, Lactobacillus buchneri, Lactobacillus bulgaricus, Lactobacillus casei, Lactobacillus cellobiosus, Lactobacillus curvatus, Lactobacillus delbruekii, Lactobacillus farciminis, Lactobacillus fermentum, Lactobacillus helveticus, Lactobacillus lactis, Lactobacillus plantarum, Lactobacillus reuteri, Leuconostoc mesenteroides, Megasphaera elsdennii, Pediococcus acidilacticii, Pediococcus cerevisiae, Pediococcus pentosaceus, Propionibacterium acidipropionici, Propionibacterium freudenreichii*, and *Propionibacterium shermanii*.

For aquaculture applications, one or more nitrification enhancement agents are preferably added contemporaneously with at least one dose (or batch) of incubated bacteria solution discharged to the growing pond, as described in U.S. application Ser. No. 15/907,682 and in U.S. Pat. No. 9,908,799. Alkalinity enhancing agents, including calcium carbonate or calcified seaweed, may be added periodically, such as seasonally or as needed to reduce phosphates, and not with each dose of bacteria. The agents can be added at a higher-than-dissolution amount to provide a continuing source of alkalinity as they slowly dissolve. Slowly dissolving alkalinity enhancing agents, such as calcified seaweed, also act as a surface area modifier, providing a support surface for biofilms of nitrifying bacteria to grow and they also aid in nutrient delivery. Additionally, agents that act only as surface area modifiers (such as pieces of metal or plastic) may be added to the growing pond as needed to reduce nitrogen or phosphorous, along with a batch or dose of incubated bacteria solution and one or more alkalinity enhancing agents, but there are preferably added only once and not with each dose of incubated bacteria solution. These surface enhancement agents similarly provide a support surface for biofilms of the added bacteria to grow, which aids in faster development of the beneficial bacteria. Most preferably, around 100 pounds of such nitrification enhancement agents are added per 7.5 million gallons of growing pond, and this amount may be scaled for other growing pond volumes. Preferred dispersal methods for the nitrification enhancement agents can include the use of automated devices or manual application to the water in the growing ponds. Automated or manually operated devices useful for broadcasting or otherwise dispersing at least one nitrification enhancement agent in the form of prills, pellets or granules are commercially available and are well known to those of skill in the art. Additionally, these nitrification enhancing agents may be dispersed through a pond using the self-dispersing additive system and method, which employs effervescent materials along with the treatment agent in water soluble packaging, described in U.S. patent application Ser. No. 14/689,790 filed on Apr. 17, 2015, which is incorporated herein by reference.

Nutrient Germinant Compositions

A nutrient germinant composition according to one preferred embodiment of the invention comprises one or more L-amino acids, D-glucose (which increases the binding affinity of L-amino acids for their cognate receptors in the spore coat and is optional), D-Fructose (optional, depending on bacteria species), a biological buffer to provide the proper pH for spore germination (such as HEPES sodium salt, a phosphate buffer, or a Tris buffer), an optional source of potassium ions (such as KCl), and an industrial preservative. In another preferred embodiment, a nutrient germinant composition further comprises both D-glucose and D-fructose. It is most preferred to include a source of potassium ions, such as KCl, when both D-glucose and D-fructose are used. The use of D-fructose, a combination of D-glucose and D-fructose, and a potassium ion source are dependent on the species of bacteria as will be understood by those of ordinary skill in the art. It is preferred to use a preservative that is pH compatible with the spore composition, which has a relatively neutral pH. According to another preferred embodiment, the nutrient spore composition also comprises spores of one or more Bacillus species and preferably one or more germination inhibitors. A nutrient germinant composition comprising spores is referred to herein as a nutrient-spore composition, formula, or solution. Alternatively, spores may be separately added to the nutrient-germinant composition according to the invention at the point-of-use. When separately added, the spores are preferably part of a spore composition or spore formulation described herein, but other commercially available spore products may also be used. According to another preferred embodiment, the nutrient germinant or nutrient spore composition is in a concentrated form, most preferably as a concentrated liquid, and is diluted at the point-of-use.

Preferred L-amino acids include one or more of L-alanine, L-asparagine, L-valine, or L-cysteine. The L-amino acids can be provided in the form of any suitable source, such as their pure forms and/or a hydrolysate of soy protein. In a further embodiment of the concentrate nutrient germinant composition, L-amino acids can be provided as a hydrolysate of soy protein. When in a concentrated form, the spore composition preferably comprises a solution of one or more of the above mentioned L-amino acids in the weight range of about 8.9 to about 133.5 g/L, more preferably about 13.2 to about 111.25 g/L, and most preferably about 17.8 to about 89 g/L each; D-glucose (optional) and/or D-fructose (optional) in the weight range of about 18 to about 54 g/L each, more preferably about 27 to about 45 g/L each, and most preferably about 30 to about 40 g/L each; KCl (optional, as a source of potassium ions) in the weight range of about 7.4 to about 22.2 g/L, more preferably about 11.1 to about 18.5 g/L, and most preferably about 14 to about 16 g/L; a biological buffer, such as monosodium phosphate in a weight range of about 10 to about 36 g/L, more preferably about 15 to about 30 g/L, and most preferably about 20 to about 24 g/L and/or disodium phosphate in a weight range of about 30 to about 90 g/L, more preferably about 21.3 to about 75 g/L, and most preferably about 28.4 to about 60 g/L. A biological buffer may also comprise one or more phosphate buffers in a total amount of 10-126 g/L. One or more biological buffers aid in maintaining the nutrient germinant composition at the proper pH for spore germination, around pH 6-8. In addition to or in place of the monosodium/disodium phosphate buffer, the spore composition may comprise other phosphate buffer(s), Tris base in a weight range of about 15 to about 61 g/L, more preferably about 24 to about 43 g/L, and most preferably about 27 to about 33 g/L; or HEPES buffer in a weight range of about 32.5 to about 97.5 g/L, more preferably about 48.75 to about 81.25 g/L, and most preferably about 60 to about 70 g/L. Optionally, monopotassium phosphate may also be used as a source of potassium ions, preferably in a weight range of about 13.6 to about 40.8 g/L, more preferably about 20.4 to about 34 g/L, and most preferably about 26 to about 29 g/L. Optionally, dipotassium phosphate may also be used as a source of potassium ions, preferably in a weight range of about 8.7 to about 26.1 g/L, more preferably about 13 to about 21.75 g/L, and most preferably about 16 to about 19 g/L. According to another preferred embodiment, the amounts of KCl, monosodium phosphate, and/or disodium phosphate can be adjusted such that the pH in the nutrient germinant solution and/or nutrient-spore solution can be about 6, about 7, or about 8.

In another preferred embodiment, the nutrient germinant composition further comprises one or more industrial preservatives at a final (total) weight range of 0.8-3.3 g/L, more preferably 1.2-2.7 g/L, most preferably 1.6-2.2. The preservative(s) can be beneficial for long-term storage. Suitable preservatives include, NaCl, D-alanine, potassium sorbate, and chemical preservatives. Chemical preservatives can be preservatives with active ingredients of methyl chloro isothiazolinone (about 1.15% to about 1.18% v/v) and methyl isothiazolinone (about 0.35-0.4% v/v); preservatives with the active ingredients of diazolidinyl urea (about 30%), methylparaben (about 11%), and propylparaben (about 3%); and preservatives with only the active ingredient of methylparaben; and other preservatives with the methyl paraben, propylparaben, and diazolidinyl urea). Non-limiting examples of chemical preservatives with methyl chloro isothiazolinone and methyl isothiazolinone as active ingredients are Linguard ICP and KATHON™ CG (which has active ingredients comprising methyl chloro isothiazolinone, around 1.15-1.18% and methyl isothiazolinone, around 0.35-0.4%). A non-limiting example of a chemical preservative with diazolidinyl urea, polyparaben, and methylparaben as active ingredients includes Germaben II. Where the active ingredients of the chemical preservative are methyl chloro isothiazolinone and methyl isothiazolinone, the chemical preservative can be included in a concentrated nutrient solution at about 0.8 to about 3.3 g/L, more preferably from about 1.2 to about 2.7 g/L, and most preferably from about 1.6 to about 2.2 g/L. Where the active ingredient(s) of the chemical preservative is diazolidinyl urea, methylparaben, and/or propylparaben, the chemical preservative can be included in a concentrated nutrient solution at about 0.3 to about 1% (wt/wt). In some aspects, the amount of a chemical preservative having diazolidinyl urea, methylparaben, and propylparaben can be included in the nutrient formulation at about 10 g/L. In the case of methylparaben, the preservative can be included in a concentrated nutrient solution at about 0.27 to about 1.89 g/L, more preferably from about 0.81 to about 1.35 g/L, and most preferably from about 1.0 to about 1.18 g/L. According to another preferred embodiment, where the nutrient formulation can be used to generate a nutrient-spore formulation effective for aquaculture applications involving shrimp, or other shellfish, the preservative can include an amount of methylparaben and potassium sorbate. According to another preferred embodiment, a nutrient germinant solution can be used to generate a nutrient-spore formulation effect for plants and/or waste water, the nutrient-spore formulation can include an amount of Linguard ICP or KATHON™ CG.

According to yet another preferred embodiment, a nutrient germinant composition may further optionally comprise an osmoprotectant compound. Ectoine, a natural osmoprotectant produced by some species of bacteria, may be included in one preferred embodiment. The amount of ectoine (optional) in a concentrated nutrient germinant composition can range from about 0.625 to about 4.375 g/L, more preferably from about 1.875-3.125 g/L, and most preferably in an amount around 2-3 g/L. According to another preferred embodiment, a nutrient germinant composition may further comprise other standard ingredients including, but not limited to, surfactants that aid in the dispersal of active ingredients, additional preservatives ensure the shelf-life of the spore composition, buffers, diluents, and/or other ingredients that are typically included in a nutrient formulation and/or spore formulation.

The amounts of the above ingredients are important aspects of the invention because higher concentrations would render some ingredients insoluble and lower concentrations would be ineffective at germinating spores.

According to another preferred embodiment, a nutrient-germinant concentrate composition according to embodiments of the invention is in concentrated form and is diluted to a working solution in water, a spore composition, or any other appropriate diluent, or a combination thereof prior to germination at a point-of-use as described further below. According to various preferred embodiments, a working nutrient germinant solution may be made by diluting a concentrated nutrient germinant composition according to a preferred embodiment herein with water or other suitable diluent in a ratio between 0.01% to 50% (v/v) concentrated nutrient germinant composition to diluent, but other amounts may also be used. The concentrated nutrient germinant compositions according to the invention may diluted anywhere from 2 to $1\times10^6$ fold or any range or value therein to produce a working nutrient germinant solution. Most preferably, dilution is in a range from about 0.1 to about 10% of the concentrate and the balance water or other suitable diluent. The amounts of the above described ingredients present in a working nutrient solution (a diluted solution from a concentrated formula) may be calculated based on the dilution factor and the concentrated amounts described above.

The use of a concentrated nutrient germinant composition reduces shipping, storage, and packaging costs and makes dosing of the spore composition at the point-of-use easier. Most preferably, the concentrated nutrient germinant composition is in a liquid form, which is easier and faster to mix with diluent at the point-of-use, but solid forms such as pellets or bricks or powder may also be used. The inclusion of a general, industrial preservative in the nutrient germinant composition aids in long-term storage.

Most preferably, all ingredients in nutrient germinant compositions according to the invention or used with methods of the invention meet U.S. federal GRAS standards.

Nutrient Spore Compositions

According to another preferred embodiment, the composition is a nutrient-spore composition comprising ingredients described above for a nutrient germinant composition and spores pre-mixed together.

According to one preferred embodiment, a nutrient spore composition comprises probiotic bacteria in sterile water. More preferably, the nutrient spore composition further comprises one or more of potassium chloride, monosodium glutamate, disodium glutamate, fructose, calcium, L-alanine, D-glucose, sodium salt. Other ingredients may also be used. *Bacillus subtilis, Bacillus licheciformis*, and *Bacillus pumilus* are the most preferred bacteria for use in this embodiment of a nutrient spore composition, but other bacteria may also be used.

According to one preferred embodiment, a nutrient spore composition preferably comprises 10% to 90% by weight of one or more *Bacillus* spores or a spore blend (comprising 40-60% spore powder with one or more *Bacillus* species and 60-40% salt). According to another preferred embodiment, a nutrient spore composition comprises around 5% by weight of one or more *Bacillus* spores or a spore blend. The total concentration of spores in the nutrient spore composition can range from about $1\times10^5$ CFU/mL or spores/g to $1\times10^{14}$ CFU/mL or spores/g or any specific concentration or range therein.

A nutrient-spore composition preferably also comprises one or more germination inhibitors and/or preservatives. Preferred germination inhibitors or preservatives for a concentrated nutrient spore composition include NaCl at a relatively high concentration ranging from about 29 to about 117 g/L, more preferably from about 43 to about 88 g/L, and most preferably from about 52 to about 71 g/L; and/or D-alanine in an amount ranging from about 8 to about 116 g/L, more preferably from about 26 to about 89 g/L, and most preferably from about 40 to about 50 g/L; and/or potassium sorbate in an amount ranging from about 1.25 to about 8.75 g/L, more preferably from about 3.75 to about 6.25 g/L, and most preferably from about 4.5 to about 5.5 g. Other chemical preservatives described above with preferred nutrient germinant composition may also be used with nutrient spore compositions according to the invention. These germination inhibitors or preservatives maintain the spores in an inactive state and prevent premature germination of the spores prior to their dilution and activation at the point-of-use. The use of germination inhibitors is particularly preferred when the spore composition according to this embodiment is used with the preferred method of the invention, where germination occurs at the point-of-use. When spores are included, the amounts of other ingredients for the nutrient germinant composition described above (such as L-amino acids, biological buffers, etc.) make up the balance of the spore composition reduced proportionally to correspond to the preferred ranges described above. Preferred nutrient spore compositions are also in concentrated form and diluted to a working solution at a point-of-use as described above with respect to nutrient germinant composition and further described below.

The preferred *Bacillus* spp. spores for use in a nutrient spore composition according to preferred embodiments of the invention include the following species: *Bacillus licheniformis, Bacillus subtilis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex*, and *Bacillus sphaericus*. Other *Bacillus* spore species may also be used as will be understood by those of ordinary skill in the art. Preferably, a nutrient spore composition comprises 1 to 20 or more species of *Bacillus*, more preferably between 3 to 12 *Bacillus* species. According to another preferred embodiment, a nutrient spore composition comprises 3 strains of *Bacillus* bacteria, most preferably 2 strains of the *Bacillus* bacteria can each be a strain of the species *Bacillus licheniformis* and the third strain is a species of *Bacillus subtilis*. According to another preferred embodiment, the spores in a spore blend comprise about 80% *Bacillus licheniformis* (40% of each strain) and 20% *Bacillus subtilis*.

In another preferred embodiment, a nutrient-spore composition for use as a probiotic comprises one or more *Bacillus* strains that are probiotic in nature in that they aid in the breakdown of nutrients in the digestive tract of the consumer. The strains preferably produce one or more of the following enzymes: proteases to hydrolyze proteins, amylases to hydrolyze starches and other carbohydrates, lipases to hydrolyze fats, glycosidases to assist in the hydrolysis of glycosidic bonds in complex sugars and to assist in degradation of cellulose, cellulases to degrade cellulose to glucose, esterase which is a lipase-like enzyme, and xylanases that degrade xylan, a polysaccharide found in plant cell walls. *Bacillus* strains that produce these enzymes are well known in the art.

According to another preferred embodiment, a nutrient spore composition is in a concentrated form and is diluted with to a working solution in water or any other appropriate diluent, or a combination thereof, prior to germination at a point-of-use as described further below. According to various preferred embodiments, a working nutrient spore solution may be made by diluting a concentrated nutrient spore composition according to a preferred embodiment herein with water or other suitable diluent in a ratio between 0.01% to 50% (v/v) concentrated nutrient germinant composition to diluent, but other amounts may also be used. The concentrated nutrient spore compositions according to the invention may diluted anywhere from 2 to $1 \times 10^{13}$ fold or any range or value therein to produce a working nutrient germinant solution. Most preferably, dilution is in a range from about 0.1 to about 10% of the concentrate and the balance water or other suitable diluent. The amounts of the above described ingredients (such as L-amino acids and germination inhibitors) present in a working nutrient solution (a diluted solution from a concentrated formula) may be calculated based on the dilution factor and the concentrated amounts described above Most preferably, all ingredients in nutrient spore compositions according to the invention or used with methods of the invention meet U.S. federal GRAS standards.

Spore Compositions

A probiotic spore composition according to one preferred embodiment of the invention comprises one or more bacterial species, an optional surfactant, a thickener, and optionally one or more acidifiers, acids or salts or acids to act as a preservative. According to another preferred embodiment, a spore composition further comprises one or more prebiotics, to the extent the thickener is not also a prebiotic, or in addition to any thickener that is a prebiotic. According to another preferred embodiment, a spore composition further comprises one or more water activity reducers. Most preferably, the spore compositions according to the invention comprise various species of suspended probiotic spores, as described in more detail below. The use of these species in spore form increases the stability of the probiotics in the harsh environmental conditions that may be found near aquaculture application sites. The total concentration of spores in the spore composition can range from about $1 \times 10^5$ CFU/mL or spores/g to $1 \times 10^{14}$ CFU/mL or spores/g or any specific concentration or range therein.

A suitable thickener is included in the spore composition according to preferred embodiments. The thickener is preferably one that does not separate or degrade at varying temperatures typically found in non-climate controlled aquaculture environments. The thickener aids in stabilizing the suspension so the bacterial mixture remains homogenous and dispersed through a volume of the spore composition and does not settle out of the suspension. When used with an incubation system and aquaculture treatment methods according to preferred embodiments of the invention described herein, this ensures that the concentration of probiotic materials is evenly distributed throughout the container so that the dosage of spores delivered to an incubator remains consistent or relatively consistent (depending on the specific delivery method and control mechanism used) throughout a treatment cycle.

The most preferred thickener is xanthan gum, which is a polysaccharide composed of pentasaccharide repeat units of glucose, mannose, and glurcuronic acid and a known prebiotic. Unlike some other gums, xanthan gum is very stable under a wide range of temperatures and pH. Another preferred thickener is acacia gum, which is also a known prebiotic. Other preferred thickeners include locust bean gum, guar gum and gum arabic, which are also believed to be prebiotics. In addition to prebiotic benefits, these fibers do not bind to minerals and vitamins, and therefore, do not restrict or interfere with their absorption and may even improve absorption of certain minerals, such as calcium, by aquatic species. Other thickeners that are not considered prebiotics may also be used.

Preferred embodiments may optionally include one or more prebiotics, which are preferably used if the thickener used is not a prebiotic but may also be used in addition to a prebiotic thickener. Prebiotics are classified as disaccharides, oligosaccharides and polysaccharides, and can include Inulin, Oligofructose, Fructo-oligosaccharides (FOS), Galacto-oligosaccharide (GOS), trans-Glacto-Oligosaccharides (TOS) and Short-Chain Fructo-oligosaccharides (scFOS), soy Fructo-oligosaccharide (soyFOS), Gluco-oligosaccharides, Glyco-oligosaccharides, Lactitol, Malto-oligosaccharides, Xylo-oligosaccharides, Stachyose, Lactulose, Raffinose. Mannan-oligosaccharide (MOS) are prebiotics may not enrich probiotic bacterial populations, but will bind with and remove pathogens from the intestinal tract and are believed to stimulate the immune system.

Preferred embodiments also preferably include one or more acidifiers, acids, or salts of acids to act as a preservative or to acidify the spore composition. Preferred preservatives are acetic acid, citric acid, fumaric acid, propionic acid, sodium propionate, calcium propionate, formic acid, sodium formate, benzoic acid, sodium benzoate, sorbic acid, potassium sorbate, and calcium sorbate. Other known preservatives, preferably generally regarded as safe (GRAS) food preservatives, may also be used. Preferably, the pH of the spore composition is between about 4.0 and 7.0. More preferably it is between about 4.0 and 5.5 and most preferably around 4.5 to prevent premature germination of the spores prior to use or addition to an incubator as described below. Reducing the pH of the spore composition may also have antimicrobial activity with respect to yeast, molds, and pathogenic bacteria.

One or more water activity reducers, such as sodium chloride, potassium chloride, or corn syrup (a 70% solution of corn syrup), are optionally included in the spore composition according either preferred embodiment. The water activity reducer aids in inhibiting microorganism growth, so that the bacterial spores do not prematurely germinate while the spore composition is being stored prior to the time it is incubated for discharge to the point of use or consumption in an aquaculture, agriculture, wastewater, or environmental remediation application. They also aid in inhibiting growth of contamination microorganisms The optional surfactant is preferably one that is safe for ingestion by animals, although other surfactants may be used with other applications, such as delivery to plants. Most preferably, the surfactant is Polysorbate 80. Although any GRAS or AAFCO approved surfactants or emulsifiers may be used with either embodiment, there are concerns that some animals may not tolerate all approved surfactants well. Because the benefits of the surfactant in stabilizing the suspension so the bacterial mixture remains homogenous and does not settle out may also be achieved by the use of the thickener, it is not necessary to add the surfactant. If a surfactant is used in the spore composition according to this second embodiment, it is preferably used in about the same weight percentage range as in the first embodiment.

Preferred bacteria for use with a spore composition according to the invention are the same as those described above for a preferred nutrient spore composition. Most preferably, the bacterial species used in a spore composition are one or more species from the *Bacillus* genus. The most preferred species for the probiotic bacteria include the following: *Bacillus pumilus, Bacillus licheniformis, Bacillus amylophilus, Bacillus subtilis, Bacillus amyloliquefaciens, Bacillus coagulans, Bacillus clausii, Bacillus firmus, Bacillus megaterium, Bacillus mesentericus, Bacillus subtilis* var. *natto*, or *Bacillus toyonensis*, but any *Bacillus* species approved as a probiotic in the country of use may also be used. It is preferred that the bacteria are in spore form, as the spore form is more stable to environmental fluctuations, such as ambient temperature changes. Most preferably, the spores used in the spore compositions according to the invention are a dry powder blend that comprises around 40-60% salt (table salt) and 60-40% bacterial spores. The spores are preferably spray-dried from a liquid fermentation concentrate. Salt is used to dilute the pure spray-dried spore powder to a standard spore count in the final spore powder blend. During production fermentation, different *Bacillus* strains will grow at different rates, resulting in varying final count numbers for the fermentation batch liquor. The fermentation liquor is centrifuged to concentrate the spores in the liquor. Then, the concentrated liquor is spray-dried which results in a powder containing only *Bacillus* spores. The addition of salt to the spray-dried *Bacillus* spore powder aids in standardizing the spore blend count per gram from batch to batch. Other forms of bacterial spores or spore blends may also be used. Most preferably, the dry spore blend is pre-mixed with a portion of the water used in the spore composition, around 3-30% of the total water, and the resulting bacteria spore solution is added to the other ingredients, including the remaining water. This aids in dispersing the bacteria spores throughout the spore composition.

A probiotic spore composition according to a first preferred embodiment of the invention preferably comprises bacterial spores that provide $10^8$ cfu/ml of the spore suspension (most preferably around $1.0 \times 10^8$ to around $3.0 \times 10^8$ cfu/ml of spore composition, which, when diluted in water in an aquaculture, agriculture, wastewater, or environmental remediation application provides approximately $10^1$ to 104 cfu/ml application water), 0.00005 to 3.0% surfactant, and 0.002 to 5.0% thickener, and optionally the about 0.01 to 2.0% of one or more acids or salts of acids as a preservative, all percentages by weight of the spore composition. A probiotic spore composition according to another preferred embodiment of the invention comprises bacterial spores that provide $10^9$ cfu/ml of the spore suspension (which, when diluted in pond water provides approximately $10^1$ to $10^4$ cfu/ml pond water), about 0.1 to 5.0% thickener (preferably one that also acts as a prebiotic), about 0.05-0.5% of one or more preservatives, optionally about 0.1-20% of one or more water activity reducers, and optionally 0.1-20% of one or more acidifiers, all percentages by weight of the composition. The balance of the spore composition in both preferred embodiments is water and the percentages herein are by weight. It is preferred to use deionized or distilled water, to remove salts or outside bacteria, but tap water or other sources of water may also be used.

According to another preferred embodiment, a spore composition comprises around 1% to 10% of a bacteria spore blend containing salt and one or more of *Bacillus pumilus, Bacillus licheniformis, Bacillus amylophilus, Bacillus subtilis, Bacillus clausii, Bacillus coagulans, Bacillus firmus, Bacillus megaterium, Bacillus mesentericus, Bacillus subtilis* var. *natto*, or *Bacillus toyonensis* in spore form; around 0.3% to 1% total of one or more acids or salts of acids; around 0.2% to 0.5% of a thickener; around 0.1-0.3% sodium chloride, potassium chloride, or a combination thereof; around 0.00005% to 3.0% of a surfactant; and 86.2% to 98.4% water. According to another preferred embodiment, a spore composition comprises around 0.01% to 10% of the bacteria spore blend; around 0.1-0.33% sorbic acid, its salt, or a combination thereof; around 0.1-0.34% citric acid, its salt, or a combination thereof; around 0.1-0.33% benzoic acid, its salt, or a combination thereof; around 0.2-0.5% xanthan gum; around 0.00005% to 3.0% of a surfactant; and around 0.1-0.3% sodium chloride, potassium chloride, or a combination thereof, all percentages by weight of the composition. According to yet another preferred embodiment, a spore composition comprises around 5% bacteria spores or a spore blend; around 0.25% thickener; around 0.3% total of one or more acids or salts of acids; around 0.1% surfactant; around 0.2% sodium chloride, potassium chloride, or a combination thereof (in addition to any salt in the spore blend); and water. According to another preferred embodiment, the acids or salts of acids are one or more of potassium sorbate, sodium benzoate, and citric acid anhydrous.

Several examples of probiotic spore compositions according preferred embodiments of the invention were made and tested for different parameters. These spore compositions are set forth in Table 1 below.

TABLE 1

| Ingredient | Formula No. | | | | | | | |
|---|---|---|---|---|---|---|---|---|
| | 1 | 2 | 3 | 4 | 5 | 6 | 7 | 8 |
| Potassium Sorbate | 0.33% | 0.33% | 0.1% | 0.1% | 0.1% | 0.1% | 0.1% | 0.1% |
| Citric Acid | 0.34% | 0.34% | 0.1% | 0.1% | 5.0% | 0.1% | 0.1% | 0.1% |
| Sodium Benzoate | 0.33% | 0.33% | 0.1% | 0.1% | 0.1% | 0.1% | 0.1% | 0.1% |
| Benzoic Acid | — | — | — | 0.1% | — | 0.1% | 0.1% | — |
| Sorbic Acid | — | — | — | 0.1% | — | — | 0.1% | — |
| Sodium Propionate | — | — | — | — | 10.0% | 0.1% | — | — |
| Xanthan Gum | 0.2% | 0.2% | 0.2% | 0.3% | 0.4% | 0.4% | 0.5% | 0.5% |
| Sodium Chloride | 0.2% | 0.2% | — | 0.2% | — | 0.2% | 0.1% | 0.2% |
| Potassium Chloride | — | — | — | — | — | — | 0.1% | 0.1% |
| Spore Blend | 0.1% | 0.1% | 0.1% | 0.1% | 0.1% | 0.1% | 0.1% | 0.1% |

The balance of each spore composition is water (around 1 L in these samples). Deionized water was used in each spore composition, except spore composition No. 1, which used tap water. The percentages indicated are by weight. Each formula was targeted to have a pH between about 4.0 and 5.5, but some formulas were found to have actual pH values far less than expected. Formula No. 1 was targeted to have a pH between 5.0 and 5.5, but its actual pH was around 2.1-2.3, which is too low and may be harmful to the spores, create stability issues with packaging, and be subject to more restrictive transportation regulations. Formula No. 1 also exhibited weak thickening. Formula No. 2 is the same as No. 1, except the source of water is different. Formula No. 2 had an actual pH of around 2.2-2.3 and also exhibited weak thickening. The amount of acids and salts of acids in Formula No. 3 was decreased to raise the pH and to determine if the thickness improved while using the same amount of thickener as in Nos. 1 and 2. While Formula No. 3 was an improvement over Nos. 1 and 2, it still exhibited weak thickening and its actual pH was 6.6, over the target value range. Additional acids were added to Formula No. 4 to lower the pH and additional thickener was added. Formula No. 4 had improved thickening, but further improvements in thickening would be beneficial. The amount of acid in Formula No. 5 was substantially increased, which resulted in an actual pH of around 1.0. The amount of acid in Formula No. 6 was decreased and the thickener increased, which resulted in a spore composition that was too thick to drop. Formula No. 7 increased the thickener and amount of water activity reducers, but exhibited issues with mixing of benzoic acid and sorbic acid. The benzoic acid and sorbic acid were removed in Formula No. 8. Formula Nos. 1-7 provided $2\times10^{11}$ cfu/gm and No. 8 provided $1\times10^{11}$ cfu/gm bacteria spores. Of these sample formulas, No. 8 is the most preferred as it exhibited adequate thickening and had an actual pH of around 4.5+/−0.2, and used less spore blend.

It is preferred that the spore compositions according preferred embodiments of the invention use around 0.01% to around 0.3% bacteria spore blend and more preferably between about 0.03% to 0.1% bacteria spore blend. A reduction in the amount of spore blend used substantially reduces the costs of the spore composition. Depending on the end use application, differing amounts of spore blend may be used in the spore compositions according to the invention. For example, smaller percentages of spore blend may be used in the spore compositions for use with chickens, whereas larger percentages would be used in spore composition for use with pigs.

A spore composition according to formula No. 8 was tested for shelf-life at various temperatures. Samples of Formula No. 8 were sealed in a plastic bag, such as one used in a preferred delivery system as described below, and stored for two months at temperatures around 4-8° C. (39-46° F.), 30° C. (86° F.), and 35° C. (95° F) to simulate typical temperature ranges in which the probiotic spore composition may be stored and used in agricultural settings. At the end of the first month of the storage period, each sample was observed and tested. All three samples had a pH of around 4.5 and there was no settling, layering or change of appearance in any of the three samples, indicating that the bacteria spores remained suspended and dispersed throughout the spore composition during the storage period. None of the samples contained any fungal contamination or gram-negative bacteria contamination. At time count zero (when the samples were initially stored), each sample contained bacteria spores of around $2.12\times10^{8}$ cfu/mL. At the end of the one month storage period, the samples contained bacteria spores of around $2.09\times10^{8}$ cfu/mL spore suspension (lowest temperature sample), $1.99\times10^{8}$ cfu/mL (middle temperature sample), and 2.15 $10^{8}$ cfu/mL (high temperature sample). The bacteria counts are somewhat variable in different samples, especially thickened samples; however, these are considered to be comparable counts. Each sample was tested again after two months in storage. The samples contained bacteria spores of around $2.08\times10^{8}$ cfu/ml (lowest temperature sample); $2.01\times10^{8}$ cfu/ml (middle temperature sample); and $2.0\times10^{8}$ cfu/ml (high temperature sample). The target shelf life is around $2\times10^{8}$ cfu/ml spore suspension, so the samples are within the targeted shelf life after two months of storage. These test results demonstrate that probiotic spore compositions according to a preferred embodiment of the invention are stable over a range of temperatures, with the bacteria spores remaining viable, suspended, and dispersed throughout the spore composition. The spore blend (40-60% spore powder and 60-40% salt) used in each sample formula was the same, providing at least around $2\times10^{11}$ spores/gram. The spore species in the blend were multiple *Bacillus subtilis* and *Bacillus licheniformis* strains. The spore blend powder was premixed with 100 mL of water with stirring for 30 minutes prior to adding to the other ingredients. Premixing with water aids in mixing the spore blend with the other ingredients and dispersing the spores throughout the spore composition.

Although it is preferred to use probiotic spore compositions comprising one or more *Bacillus* species as according to the preferred spore compositions of the invention, the methods of the invention may be used with spore compositions comprising other bacteria genera and other species. For example, one or more species from the following genera: *Bacillus, Bacteroides, Bifidobacterium, Pediococcus, Enterococcus, Lactobacillus*, and *Propionibacterium* (including *Bacillus pumilus, Bacillus licheniformis, Bacillus amylophilus, Bacillus subtilis, Bacillus amyloliquefaciens, Bacillus clausii, Bacillus coagulans, Bacillus firmus, Bacillus megaterium, Bacillus mesentericus, Bacillus subtilis* var. *natto*, or *Bacillus toyonensis Bacteroides ruminocola, Bacteroides ruminocola, Bacterioides suis, Bifidobacterium adolescentis, Bifidobacterium animalis, Bifidobacterium bifidum, Bifidobacterium infantis, Bifidobacterium longum, Bifidobacterium thermophilum, Pediococcus acidilacticii, Pediococcus cerevisiae, Pediococcus pentosaceus, Enterococcus cremoris, Enterococcus diacetylactis, Enterococcus faecium, Enterococcus intermedius, Enterococcus lactis, Enterococcus thermophilus, Lactobacillus delbruekii, Lactobacillus fermentum, Lactobacillus helveticus, Lactobacillus lactis, Lactobacillus plantarum, Lactobacillus reuteri, Lactobacillus brevis, Lactobacillus buchneri, Lactobacillus bulgaricus, Lactobacillus casei, Lactobacillus farciminis, Lactobacillus cellobiosus, Lactobacillus curvatus, Propionibacterium acidipropionici, Propionibacterium freudenreichii, Propionibacterium shermanii*) and/or one or more of the following species: *Leuconostoc mesenteroides, Megasphaera elsdennii* may be used with compositions and method of the invention.

Spore compositions may also be in a concentrated form, using less water with a proportional increase in the amounts of other ingredients as described above. Such concentrated spore compositions may be diluted at the point-of-use with a nutrient germinant composition, water, other suitable diluent or a combination thereof prior to germination. Most preferably, all ingredients in spore compositions according to preferred embodiments of the invention or used with preferred methods of the invention meet U.S. federal GRAS standards.

Methods of Germination According to one preferred embodiment, a method of germinating spores at a point-of-use according to the invention comprises providing nutrients and spores (preferably providing a nutrient germinant composition and a spore composition or providing a nutrient spore composition according to the invention, but other commercially available products containing spores and nutrients, together or separately, may be used) and heating them to an elevated temperature or range of temperatures and maintaining them at that temperature or within that range for a period of time (incubation period) using a flameless heater to allow germination at a point-of-use location near a point-of-consumption. Heating during the incubation period takes place in a single step with both the nutrients and spores together. The method also preferably comprises the step of dispensing the germinated spores to an aquaculture, agriculture, wastewater, or environmental remediation application as previously discussed. Preferably, the nutrient germinant composition and spore composition (or nutrient spore composition) are heated to a temperature in a range of 38° C. to around 90° C., more preferably 35-55° C., even more preferably in the range of 38-50° C. or 38-60° C., and most preferably in the range of 41° C. to 44° C. with heat supplied from an exothermic chemical reaction. The incubation period can vary depending on the end-use application. For a probiotic application, where the aquatic species with a digestive system (e.g. fish or eels) will ingest the bacteria, it is preferred that the incubation period lasts no longer than 10 minutes. Most preferably, in a probiotic application, the incubation period is between 2-5 minutes. In this way, spores are released to the aquaculture or agriculture, before the spores have fully germinated and stand a better chance of surviving through to ingesting species' intestinal tract where they are most beneficial. For treating the water in an aquaculture application, such as may be done with a shrimp aquaculture application, or a wastewater application, the preferred incubation time is at least one hour to allow the spores to fully germinate before discharging to the water, more preferably 4 to 6 hours, to allow the bacteria to become vegetative before discharging to the water. Most preferably, a nutrient germinant composition and a spore composition (or a nutrient spore composition), preferably in accordance with an embodiment of the invention discussed herein, are added to an incubator to incubate the spores at the above preferred temperature ranges and durations to produce a bacteria solution having bacteria in a vegetative state. The incubation is preferably in a container, tank or reservoir containing a nutrient germinant composition and spores that is heated to within the desired range using a flameless heater. The bacteria solution is then discharged to an aquaculture application as previously discussed. If a concentrated nutrient germinant composition is used, diluent water is preferably added to the incubator with the nutrient germinant composition.

Various nutrient germinant compositions according to preferred embodiments of the invention were tested according to preferred methods of the invention. The compositions, methods, and results are described below.

Example 1

To germinate spores, FreeFlow LF-88 Probiotic (spore liquid formula commercially available from NCH Corporation) was added to 1 mL of tap water at a final concentration of approx. $1 \times 10^9$ CFU/mL, where CFU stands for colony forming unit. A nutrient germinant concentrate composition according to a preferred embodiment of the invention comprising L-alanine (89 g/L), monosodium phosphate (20 g/L), disodium phosphate (60 g/L), and Linguard CP (1.6 g/L total) was added to the water and bacteria mixture to provide a 4% final concentration of nutrient-germinant composition by total weight of the mixture. For comparison, negative control reactions were prepared with the same amount of FreeFlow LF-88 Probiotic and water, but without adding the nutrient germinant concentrate composition. Both mixtures (germinant and negative control without the nutrient-germinant composition) were blended and incubated for 60 minutes in a pre-incubated heat block set to 42° C. or at ambient room temperature (around 23° C.).

Spores from each reaction were observed using phase contrast microscopy. Slides were prepared using standard procedures. Spores were viewed on an Olympus BX41 microscope (100× oil emersion objective) and imaged using an Olympus UC30 camera controlled by the cellSens Dimension software package.

Images were taken and germinated spores were counted as a percentage of the total spores in the field. A total of 10 representative images were analyzed for each condition (test mixture). Germinated spores lose their refractivity due to the influx of water and are phase-dark while non-germinated spores are phase-bright.

Figure 5:
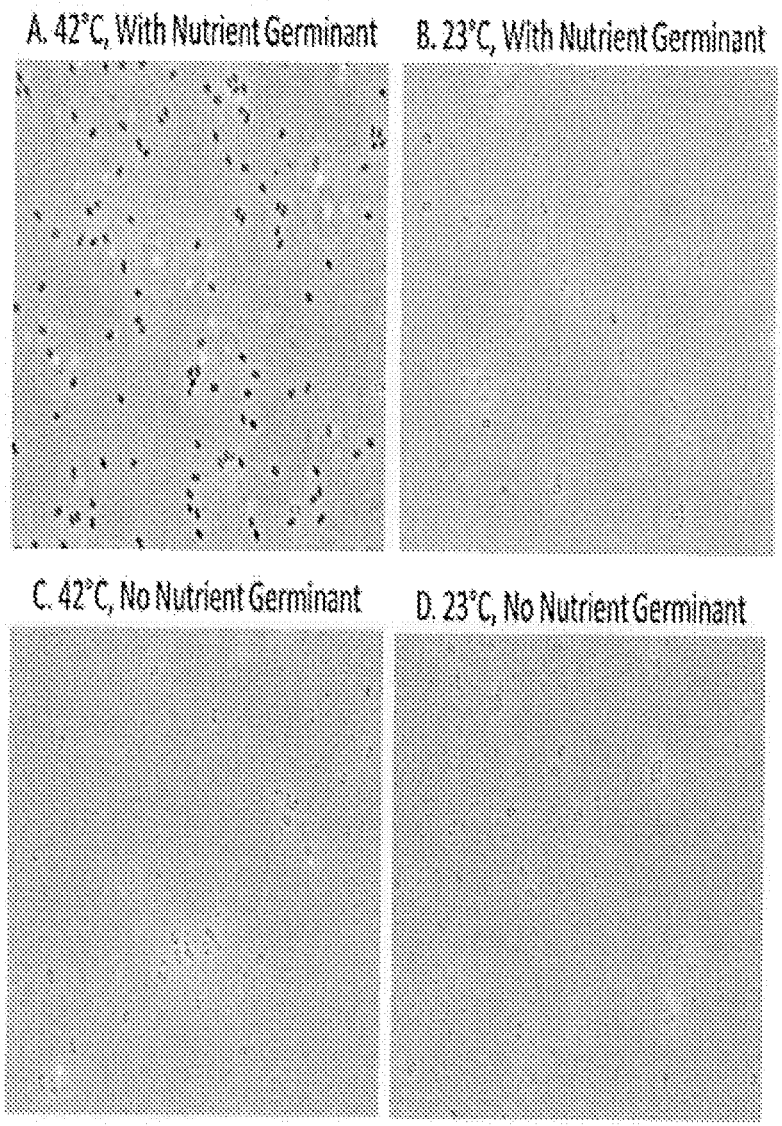
FIG. 5 shows photographs of bacteria slides using a spore composition and method according to a preferred embodiment of the invention compared to control slides.

FIG. 5 shows representative images from these tests. Image A represents spores that had been germinated using a nutrient-germinant composition and heated during the incubation period at 42° C. according to a preferred spore composition and preferred method of the invention. The darker spots show germinated spores, the lighter spots show non-germinated spores. Image B represents spores that had been germinated using a nutrient-germinant composition according to a preferred embodiment of the invention, but were incubated at ambient temperature (23° C.). Images C-D represent control spores that had not been treated with a nutrient germinant composition according to the invention, one having been incubated at 42° C. and one incubated at ambient temperature (23° C.).

As can be seen in FIG. 5, the "A" image shows significantly more germinated spores (dark spots) than the other images. Spores incubated with a nutrient-germinant composition according to a preferred embodiment invention in combination with a germination method according to a preferred embodiment of the invention show an apparent germination efficiency of 96.8% (Example 1, FIG. 5A). Control spores that had been incubated with a nutrient-germinant composition according to a preferred embodiment of the invention, but without using a germination method according to a preferred embodiment of the invention showed an apparent germination efficiency of 2.3% (Example 1, FIG. 5B). Similarly, spores that had not been incubated with a nutrient-germinant composition according to the invention showed an apparent activation efficiency of 1.2% and 2.6% at 42° C. and 23° C., respectively (Example 1, FIGS. 5C and 5D). Germinated spores in the samples not treated by preferred embodiments of the present method represent the small percentage of spores already germinated in the FreeFlow LF-88 Probiotic solution. This example demonstrates that spore germination is significantly increased when a nutrient-germinant composition and incubation method according to preferred embodiments of the invention are used together.

Example 2

Another set of incubation tests were run using the same test mixture/incubation method (using the same nutrient-germinant composition and heated incubation, "Treated Spores, 42° C.") and control mixture/incubation method (no nutrient-germinant composition and no heat, "Non-treated Spores, 23° C.") as described above in Example 1 were repeated, but different tests were run to compare the efficacy of the test mixture according to preferred embodiments of the invention as compared to the control mixture. Additionally, two other mixtures were tested—one in which the nutrient-germinant composition of Example 1 was used but without heat ("Treated Spores, 23° C.") and one in which no nutrient-germinant was used but the spores were heated ("Non-Treated Spores, 42° C."). Briefly, spores were incubated at 42° C. or 23° C. for 1 hour with or without treatment with a preferred nutrient-germinant composition. After incubation, the spores from 1 mL of each reaction were pelleted at 14K RPM for 3 min at 23° C. and resuspended in 1 mL of Butterfield's buffer. Approx. 6×10$^5$ CFUs (0.02 mL) were added to 0.980 mL of Davis minimal media (containing 3% glucose as a carbon source and trace elements) with an excess of D-alanine. D-alanine is a potent inhibitor of L-amino acid-mediated germination.

Approx. 1.2×10$^5$ CFUs were added to each of four wells of a PreSens OxoPlate. PreSens OxoPlates use optical oxygen sensors to fluorescently measure the oxygen content of the sample using two filter pairs (excitation: 540 nm, emission: 650 nm and excitation: 540, emission: 590 nm). Controls were performed as described by the manufacturer and measurements were taken on a BioTek 800FLx fluorescence plate reader. Time points were taken every 10 minutes for 24 hours at 37° C. with continual shaking and data was processed to determine the partial pressure of oxygen (pO$_2$) using the following formula:

$$pO_2 = 100*[(K_0/IR) - 1(K_0/K_{100}) - 1]$$

Spores that have germinated and continue to divide and grow as vegetative cells consume oxygen as part of their metabolic growth. Oxygen consumption is represented by a drop in pO$_2$. Presumably, the growth that is observed is due to the outgrowth and vegetative growth of spores germinated by the present invention. The pO$_2$ levels for these tests are shown in FIG. 6.

Figure 6:
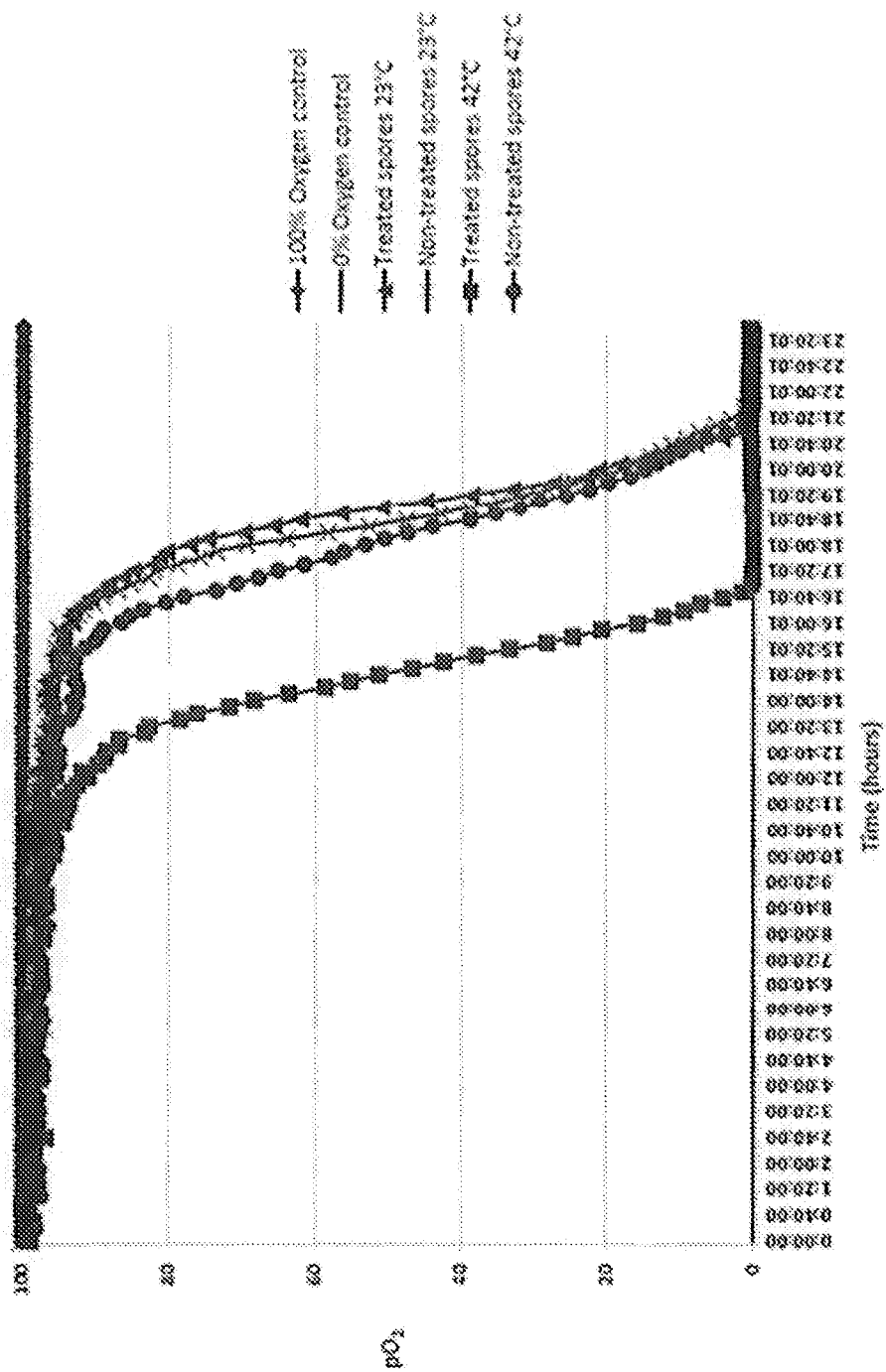
FIG. 6 is a graph showing $pO_2$ test data to demonstrate germination levels using a spore composition and method according to a preferred embodiment of the invention compared to control tests.

As shown in FIG. 6, incubation with the test mixture and method according to preferred embodiments of the invention (Treated spores 42° C., using both the nutrient-germinant composition and heating) resulted in spores that began vegetative growth 4 hours faster than the control spore mixtures that had not been treated or heated according to preferred embodiments of the invention or had been either treated with a nutrient-germinant composition or heated, but not both together. The growth seen in the control experiments presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

Example 3

Another set of incubation tests were run using a similar test and control mixture and incubation method as described above in Example 1. Briefly, LF-88 was added to 10 mLs of distilled water at a final concentration of approx. 10$^8$ CFU/mL. Samples were incubated at various temperatures to show the efficacy of the test method according to preferred embodiments of the invention as compared to the control mixture. Reactions were prepared with the nutrient-germinant composition described in Example 1 ("Treated spores" in FIG. 7) and incubated at 23° C. (ambient temperature, no heating), 32° C., 42° C., or 60° C. A control reaction was incubated at ambient room temperature with no nutrient-germinant composition. After one hour of incubation, 1 mL of each reaction was pelleted at 14K RPM for 3 min at 23° C. and resuspended in Butterfield's buffer. Approx 6×10$^5$ CFUs (0.02 mL) were added to 0.980 mL of Davis minimal media (containing 3% glucose as a carbon source and trace elements) with an excess of D-alanine.

Approx. 1.2×10$^5$ CFUs were added to each of four wells of a PreSens OxoPlate. Controls were performed as described by the manufacturer and measurements were taken on a BioTek 800FLx fluorescence plate reader using two filter pairs (excitation: 540 nm, emission: 650 nm and excitation: 540, emission: 590 nm). Time points were taken every 10 minutes for 24 hours at 37° C. with continual shaking and data was processed to determine the partial pressure of oxygen (pO$_2$). The pO$_2$ levels for these tests are shown in FIG. 7.

Figure 7:
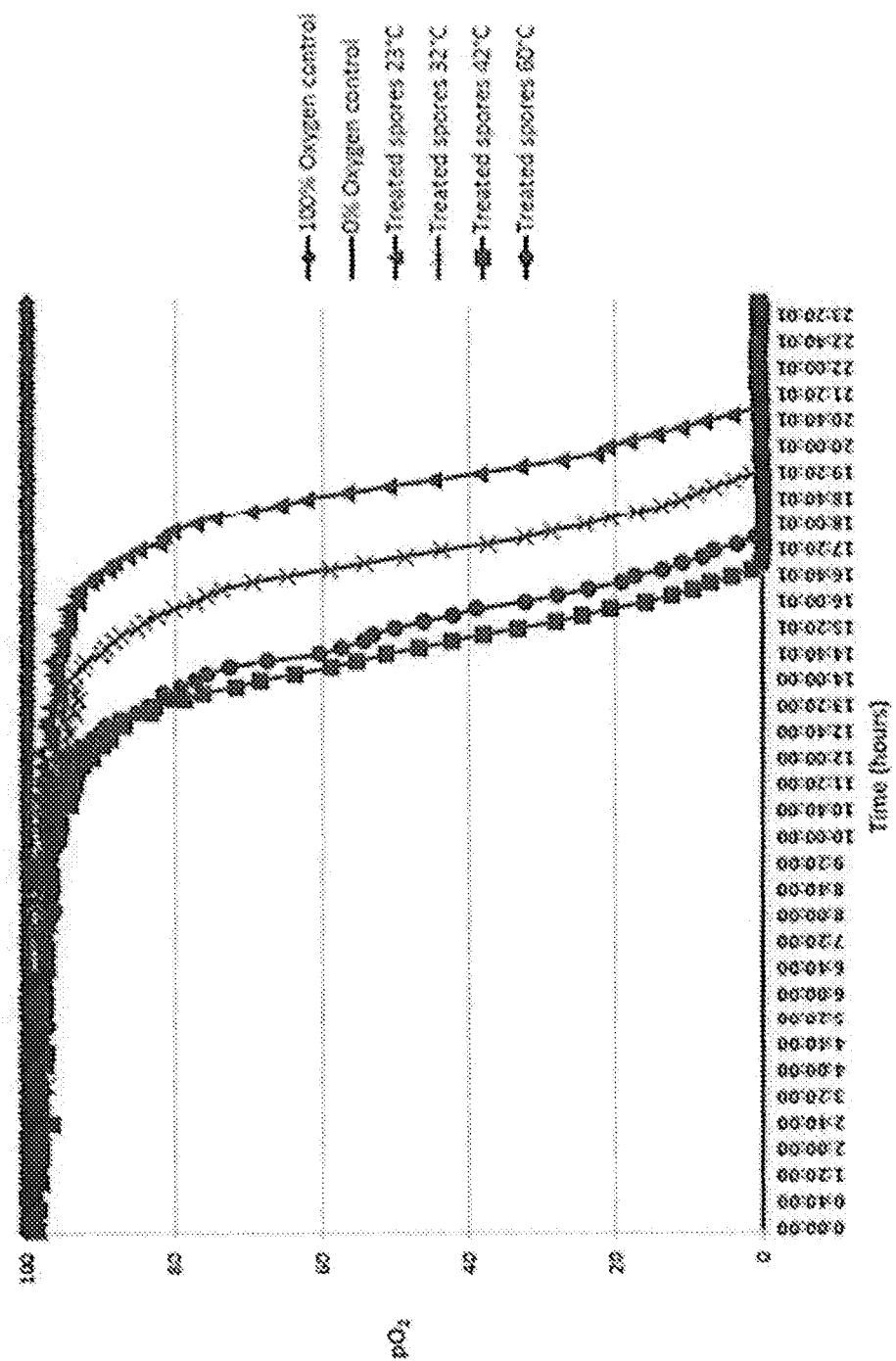
FIG. 7 is a graph showing $pO_2$ test data to demonstrate germination levels using a spore composition and varied methods according to preferred embodiments of the invention compared to control tests.

As shown in FIG. 7, incubation using a nutrient-germinant composition and heating according to preferred embodiments of the invention resulted in spores that began vegetative growth hours before the control. Spores treated with the nutrient-germinant composition but not heated are comparable to the control mixture. Spores treated with the nutrient-germinant composition that were incubated at a temperature below the preferred range of range of 35-55° C. according to one embodiment of the invention (represented by the "Treated spores 32° C." curve) begin vegetative growth faster than control experiments, but not as fast as spores treated at elevated temperatures within the preferred ranges according to the invention. Spores treated with a nutrient-germinant composition and incubated at a temperature within the most preferred range of 41° C. to 44° C. according to an embodiment of the invention showed the best results, being the first to begin vegetative growth and beginning growth 4 hours faster than the control. As seen in previous examples, growth seen in the no-treatment control experiment presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

According to other preferred embodiments, a method of adding bacteria to water used in an aquaculture, agriculture, wastewater, or environmental remediation application comprises: (1) providing a volume of nutrient germinant composition and a volume of a bacteria comprising at least one species in spore form, which may be premixed together as a nutrient spore composition or separate; (2) optionally mixing a portion of the nutrient germinant composition and a portion of the bacteria if separate to form the nutrient spore composition; (3) initiating an exothermic chemical reaction in a flameless heater; (4) heating at least a portion of the nutrient spore composition to a temperature in a range of around 35° C. to 60° C. at or near a site of the aquaculture application using heat generated by the exothermic reaction; (5) maintaining the temperature in the range for an incubation period of around 2 minutes to around 6 hours to form a batch of incubated bacteria solution; and (6) discharging the incubated bacteria solution to an aquaculture, agriculture, wastewater, or environmental remediation application. Most preferably, the exothermic reaction in step (3) is initiated by adding water, air, or a second chemical to a first chemical that exothermically reacts with the water, air, or second chemical and the first chemical is magnesium 5 atomic weight percent iron supercorroding alloy and the exothermic reaction is initiated by adding water. Most preferably, the nutrient germinant composition is in a first sealed packet and the spore composition is in a second sealed packet or the nutrient germinant composition and spore composition are premixed together as a nutrient spore composition in a third sealed packet, and the method further comprises: (7) providing a sealable mixing container if the nutrient germinant composition and spore composition are not premixed; (8) providing an incubation container configured to hold the flameless heater and the mixing container or the third sealed packet; (9) emptying the contents of the first sealed packet and second sealed packet into the mixing container and sealing the mixing container if the nutrient germinant composition and spore composition are not premixed; (10) prior to or during the exothermic reaction, placing (a) the third packet inside the incubation container, if not already inside the incubation container or (b) the mixing container inside the incubation container; and wherein the discharging step comprises removing the third sealed packet or sealed mixing container, opening the third packet or mixing container, and manually applying the incubated bacteria solution to aquaculture, agriculture, wastewater, or environmental remediation application.

Preferably, the bacteria in these embodiments comprises one or more of the genera *Bacillus, Bacteroides, Bifidobacterium, Lueconostoc, Pediococcus, Enterococcus, Lactobacillus, Megasphaera, Pseudomonas* and *Propionibacterium*. More preferably, the bacteria are one or more species of *Bacillus licheniformis* and *Bacillus subtilis* or wherein the bacteria is probiotic bacteria selected from the group consisting of *Bacillus amylophilus, Bacillus licheniformis, Bacillus pumilus, Bacillus subtilis, Bacteroides ruminocola, Bacteroides ruminocola, Bacterioides suis, Bifidobacterium adolescentis, Bifidobacterium animalis, Bifidobacterium bifidum, Bifidobacterium infantis, Bifidobacterium longum, Bifidobacterium thermophilum, Enterococcus cremoris, Enterococcus diacetylactis, Enterococcus faecium, Enterococcus intermedius, Enterococcus lactis, Enterococcus thermophiles, Lactobacillus brevis, Lactobacillus buchneri, Lactobacillus bulgaricus, Lactobacillus casei, Lactobacillus cellobiosus, Lactobacillus curvatus, Lactobacillus delbruekii, Lactobacillus farciminis, Lactobacillus fermentum, Lactobacillus helveticus, Lactobacillus lactis, Lactobacillus plantarum, Lactobacillus reuteri, Leuconostoc mesenteroides, Megasphaera elsdennii, Pediococcus acidilacticii, Pediococcus cerevisiae, Pediococcus pentosaceus, Propionibacterium acidipropionici, Propionibacterium freudenreichii*, and *Propionibacterium shermanii.*

Preferably, the nutrient germinant composition or premixed nutrient spore composition in these embodiments comprises: an L-amino acid; one or more buffers comprising a phosphate buffer, HEPES, Tris base, or a combination thereof; an industrial preservative; optionally D-glucose, or optionally D-fructose, or optionally both D-glucose and D-fructose; and optionally a source of potassium ions. More preferably, the nutrient germinant composition or premixed nutrient spore composition comprises around 17.8 g/L to 89 g/L total of one or more of L-alanine, L-asparagine, L-valine, L-cysteine, a hydrolysate of soy protein, or a combination thereof. Additionally, the premixed nutrient spore composition in these embodiments preferably further comprises spores of a *Bacillus* species and a germination inhibitor or preservative comprising sodium chloride, D-alanine, or a combination thereof. Preferably, the nutrient germinant composition, or nutrient spore composition if premixed, used in these embodiments is a concentrated liquid comprising: around 8.9-133.5 g/L of one or more L-amino acids; around 0.8-3.3 g/L total of the one or more industrial preservatives; around 40-126 total of one or more phosphate buffers, around 15-61 g/L Tris base, or around 32.5-97.5 g/L HEPES, or a combination thereof; optionally around 18-54 g/L of D-glucose, D-fructose, or a combination thereof; optionally around 7.4-22.2 g/L of KCl; and optionally one or more bacteria species in spore form. Preferably, the spore composition used in these embodiments comprises: one or more *Bacillus* species in spore form; about 0.002 to 5.0% by weight thickener; about 0.01 to 2.0% by weight total of one or more acids or salts of acids; and optionally about 0.00005 to 3.0% by weight of a surfactant, wherein the percentages are by weight of the spore composition. More preferably, the spore composition has a pH of around 4.5 to around 5.5 and/or the acids or salts of acids are one or more of acetic acid, citric acid, fumaric acid, propionic acid, sodium propionate, calcium propionate, formic acid, sodium formate, benzoic acid, sodium benzoate, sorbic acid, potassium sorbate, or calcium sorbate. Still more preferably, the spore composition comprises: about 0.002 to 5.0% by weight thickener; about 0.01 to 2.0% by weight total of one or more acids or salts of acids; and optionally about 0.00005 to 3.0% by weight of a surfactant.

According to other preferred embodiments, a system for generating an incubated bacteria solution for use in an aquaculture, agriculture, wastewater, or environmental remediation application comprises: (1) a first container having a volume of nutrient germinant composition and a second container having a volume of spore composition and a third container for mixing at least a portion of the nutrient germinant composition from the first container and at least a portion of the spore composition from the second container or (2) a fourth container having a premixed nutrient spore composition; and a flameless heater disposed near the third container or fourth container, the flameless heater comprising a first chemical that exothermically reacts with a second chemical, water, or air to heat the contents of the third container or fourth container to a temperature in a range of around 35° C. to 90° C. for an incubation period to generate an incubated spore solution. Preferably, the system further comprises a fifth container configured to hold the flameless heater and the third container or the fourth container; and wherein (1) the first and second containers are sealed packets and the third container is sealable or (2) the fourth container is a sealed packet. Most preferably, the fifth container comprises markings indicating a fill-line for adding water to the fifth container and/or a divider forming a first part for holding the flameless heater and a second part for holding the sealed third container or fourth packet so that the flameless heater does not directly contact the sealed third container or fourth packet and/or is made from transparent material. Preferably, the third container or fourth packet are made of insulating materials and/or the divider of the fifth container is made of insulating materials. Preferably, incubation period is around 2 minutes to six hours. Preferably, the flameless heater in these embodiments further comprises a water and gas permeable pouch containing the first chemical or a divided pouch having first and second parts or a first pouch contained within a second pouch; wherein the first part or first pouch contains the first chemical and the second part of second pouch contains the second chemical. Preferably, the fifth container in these embodiments is sealed with a vacuum seal or is filled with non-reactive gas and the first chemical reacts with air when the fifth container is opened.

Any ingredient, feature, or step of a preferred embodiment herein may be used with any other ingredients, features, or steps of other embodiments even if not specifically described with respect to that embodiment. All amounts for ingredients or ratios of ingredients indicated herein as a range include each individual amount or ratio within those ranges and any and all subset combinations within ranges, including subsets that overlap from one preferred range to a more preferred range and even if the specific subset of the range is not specifically described herein. Any ingredient or amount of an ingredient described as included or excluded with any particular preferred embodiment herein may similarly be included or excluded with any other preferred embodiment herein even if not specifically described with such embodiment. Those of ordinary skill in the art will also appreciate upon reading this specification and the description of preferred embodiments herein that modifications and alterations to the methods and nutrient germinant and spore compositions may be made within the scope of the invention and it is intended that the scope of the invention disclosed herein be limited only by the broadest interpretation of the appended claims to which the inventors are legally entitled.

What is claimed is:

1. A system for generating an incubated bacteria solution for use in an aquaculture, agriculture, wastewater, or environmental remediation application, the system comprising:
   a flameless heater comprising a first chemical that exothermically reacts and is configured to heat the nutrient-spore composition to a temperature in a range of around 35° C. to 90° C. for an incubation period to generate an incubated spore solution; and
   a container comprising a divider forming a first part in which the flameless heater is disposed and a second part configured to hold the nutrient-spore composition so that the flameless heater does not directly contact the nutrient-spore composition; and
   wherein the first part of the container is sealed with a vacuum seal or is filled with non-reactive gas and the first chemical reacts with air when the first part of the container is opened.

2. The system of claim 1 wherein the second part of the container comprises markings indicating a fill-line for adding water to the container.

3. The system of claim 1 wherein the container is insulated.

4. The system of claim 1 wherein the divider is made of insulating materials.

5. The system of claim 1 wherein the incubation period is around 2 minutes to six hours.

6. The system of claim 1 wherein the flameless heater further comprises a gas permeable pouch containing the first chemical.

7. A system for generating an incubated bacteria solution for use in an aquaculture, agriculture, wastewater, or environmental remediation application, the system comprising:
   one or more containers configured to hold (1) a volume of a nutrient-germinant composition and a separate volume of a spore composition that are mixable to form a nutrient-spore composition or (2) the nutrient-spore composition in a pre-mixed form;
   a flameless heater disposed near the container configured to hold the nutrient-spore composition comprising a first chemical that exothermically reacts and is configured to heat the nutrient-spore composition to a temperature in a range of around 35° C. to 90° C. for an incubation period to generate an incubated spore solution;
   an incubator comprising a divider forming a first part in which the flameless heater is disposed and a second part in which the container configured to hold the nutrient-spore composition is disposed;
   wherein the first part of the divided incubator is sealed with a vacuum seal or is filled with non-reactive gas and the first chemical reacts with air when the first part of the divided container is opened;
   wherein the incubator or container configured to hold the nutrient-spore composition is configured so that the flameless heater and byproducts of the exothermic reaction do not directly contact the nutrient-spore composition.

8. The system of claim 7 wherein the container configured to hold the nutrient-spore composition is sealed.

9. The system of claim 1 further comprising the nutrient germinant composition, which comprises a spore composition and a nutrient germinant composition, wherein the spore composition comprises:
   one or more *Bacillus* species in spore form;
   about 0.002 to 5.0% by weight thickener;
   about 0.01 to 2.0% by weight total of one or more acids or salts of acids; and
   optionally about 0.00005 to 3.0% by weight of a surfactant;
   wherein the percentages are by weight of the spore composition; and
   wherein the acids or salts of acids are one or more of acetic acid, citric acid, fumaric acid, propionic acid, sodium propionate, calcium propionate, formic acid, sodium formate, benzoic acid, sodium benzoate, sorbic acid, potassium sorbate, or calcium sorbate.

10. The system of claim 1 further comprising the the nutrient-spore composition, wherein the nutrient-spore composition is a concentrated liquid comprising:
    around 8.9-133.5 g/L of one or more L-amino acids;
    around 0.8-3.3 g/L total of the one or more industrial preservatives;
    around 40-126 g/L total of one or more phosphate buffers, around 15-61 g/L Tris base, or around 32.5-97.5 g/L HEPES, or a combination thereof;
    optionally around 18-54 g/L of D-glucose, D-fructose, or a combination thereof; and
    optionally around 7.4-22.2 g/L of KCl.

11. A method of adding bacteria to water used in an aquaculture, agriculture, wastewater, or environmental remediation application, the method comprising:
    providing a container comprising a divider forming a first part containing a flameless heater and a second part containing a nutrient-spore composition so that the flameless heater does not directly contact the nutrient-spore composition, the flameless heater comprising a first chemical that exothermically reacts;
    initiating an exothermic chemical reaction in the flameless heater;
    heating the nutrient spore composition to a temperature in a range of around 35° C. to 90° C. at or near a site of the application using heat generated by the exothermic reaction;
    maintaining the temperature in the range for an incubation period of around 2 minutes to around 6 hours to form a batch of incubated bacteria solution; and
    discharging the incubated bacteria solution to an aquaculture, agriculture, wastewater, or environmental remediation application;
    wherein the first part of the container is sealed with a vacuum seal or is filled with non-reactive gas; and wherein the first chemical reacts with air when the first part of the container is opened.

12. The method of claim 1 further comprising:
mixing at least a portion of a volume of a nutrient germinant composition and at least a portion of a volume of a spore composition to form the nutrient-spore composition.

13. The method of claim 11 wherein the nutrient-spore composition comprises one or more of the genera *Bacillus, Bacteriodes, Bifidobacterium, Lueconostoc, Pediococcus, Enterococcus, Lactobacillus, Megasphaera, Pseudomonas* and *Propionibacterium*.

14. The method of claim 11 wherein the nutrient-spore composition comprises one or more species of *Bacillus licheniformis* and *Bacillus subtilis* in spore form.

15. The method of claim 11 wherein the nutrient-spore composition comprises probiotic bacteria selected from the group consisting of *Bacillus amylophilus, Bacillus licheniformis, Bacillus pumilus, Bacillus subtilis, Bacteriodes ruminocola, Bacteriodes ruminocola, Bacterioides suis, Bifidobacterium adolescentis, Bifidobacterium animalis, Bifidobacterium bifidum, Bifidobacterium infantis, Bifidobacterium longum, Bifidobacterium thermophilum, Enterococcus cremoris, Enterococcus diacetylactis, Enterococcus faecium, Enterococcus intermedius, Enterococcus lactis, Enterococcus thermophiles, Lactobacillus brevis, Lactobacillus buchneri, Lactobacillus bulgaricus, Lactobacillus casei, Lactobacillus cellobiosus, Lactobacillus curvatus, Lactobacillus delbruekii, Lactobacillus farciminis, Lactobacillus fermentum, Lactobacillus helveticus, Lactobacillus lactis, Lactobacillus plantarum, Lactobacillus reuteri, Leuconostoc mesenteroides, Megasphaera elsdennii, Pediococcus acidilacticii, Pediococcus cerevisiae, Pediococcus pentosaceus, Propionibacterium acidipropionici, Propionibacterium freudenreichii,* and *Propionibacterium shermanii*.

16. The method of claim 11 wherein the nutrient-spore composition comprises:
an L-amino acid;
one or more buffers comprising a phosphate buffer, HEPES, Tris base, or a combination thereof;
an industrial preservative;
optionally D-glucose, or optionally D-fructose, or optionally both D-glucose and D-fructose; and
optionally a source of potassium ions.

17. The method of claim 16 wherein the nutrient-spore composition comprises around 17.8 g/L to 89 g/L total of one or more of L-alanine, L-asparagine, L-valine, L-cysteine, a hydrolysate of soy protein, or a combination thereof.

18. The method of claim 16 wherein the nutrient-spore composition comprises spores of a *Bacillus* species and further comprises sodium chloride, D-alanine, or a combination thereof.

19. The method of claim 18 wherein the nutrient-spore composition comprises around 29 g/L to 117 g/L sodium chloride or around 8 g/L to 116 g/L D-alanine, or both.

20. The method of claim 8 wherein the phosphate buffer comprises around 10-36 g/L of monosodium phosphate and around 30-90 g/L of disodium phosphate.

21. The method of claim 12 wherein the volume of nutrient germinant composition is in a first sealed packet and the volume of the spore composition is in a second sealed packet, the method further comprising;
emptying the contents of the first sealed packet and second sealed packet into the container to form the nutrient-spore composition in the container; and
optionally sealing the container prior to the heating step.

22. The method of claim 11 wherein the nutrient-spore composition is a concentrated liquid comprising:
around 8.9-133.5 g/L of one or more L-amino acids;
around 0.8-3.3 g/L total of the one or more industrial preservatives;
around 40-126 total of one or more phosphate buffers, around 15-61 g/L Tris base, or around 32.5-97.5 g/L HEPES, or a combination thereof;
optionally around 18-54 g/L of D-glucose, D-fructose, or a combination thereof;
optionally around 7.4-22.2 g/L of KCl; and
wherein the method further comprises diluting the nutrient spore composition prior to or during the heating step.

23. The method of claim 12 wherein the spore composition comprises:
one or more *Bacillus* species in spore form;
about 0.002 to 5.0% by weight thickener;
about 0.01 to 2.0% by weight total of one or more acids or salts of acids; and
optionally about 0.00005 to 3.0% by weight of a surfactant;
wherein the percentages are by weight of the spore composition.

24. The method of claim 23 wherein the spore composition has a pH of around 4.5 to around 5.5.

25. The method of claim 23 wherein the acids or salts of acids are one or more of acetic acid, citric acid, fumaric acid, propionic acid, sodium propionate, calcium propionate, formic acid, sodium formate, benzoic acid, sodium benzoate, sorbic acid, potassium sorbate, or calcium sorbate.

26. The method of claim 24 wherein the spore composition comprises:
about 0.002 to 5.0% by weight thickener;
about 0.01 to 2.0% by weight total of one or more acids or salts of acids; and
optionally about 0.00005 to 3.0% by weight of a surfactant;
wherein the percentages are by weight of the spore composition.

27. The method of claim 11 wherein the incubation period is around 2 minutes to around 5 minutes when the nutrient-spore composition comprised probiotic bacteria are used.

28. The method of claim 11 wherein the incubation period is around 4 to 6 hours.

29. The method of claim 11 wherein the incubated bacteria solution comprises metastable state bacteria and the incubation period is around 2 to 5 minutes.

30. The method of claim 11 wherein the incubated bacteria solution comprises active bacteria and the incubation period is around 20 to 60 minutes.

* * * * *